US012767571B2

(12) United States Patent
Miyamoto et al.

(10) Patent No.: US 12,767,571 B2
(45) Date of Patent: Oct. 20, 2026

(54) AROMATIC POLYESTER-DEGRADING BACTERIA

(71) Applicant: JEPLAN, INC., Kawasaki (JP)

(72) Inventors: Kenji Miyamoto, Yokohama (JP); Yuki Kawai, Kawasaki (JP); Masakazu Kadoyama, Kawasaki (JP)

(73) Assignee: JEPLAN, INC., Kawasaki (JP)

( * ) Notice: Subject to any disclaimer, the term of this patent is extended or adjusted under 35 U.S.C. 154(b) by 359 days.

(21) Appl. No.: 18/578,814

(22) PCT Filed: Jun. 28, 2022

(86) PCT No.: PCT/JP2022/025831

§ 371 (c)(1),
(2) Date: Jan. 12, 2024

(87) PCT Pub. No.: WO2023/286593

PCT Pub. Date: Jan. 19, 2023

(65) Prior Publication Data

US 2024/0336506 A1 Oct. 10, 2024

(30) Foreign Application Priority Data

Jul. 13, 2021 (JP) ................................ 2021-115744

(51) Int. Cl.

| | |
|---|---|
| ***C02F 103/38*** | (2006.01) |
| ***C02F 3/10*** | (2023.01) |
| ***C02F 3/12*** | (2023.01) |
| ***C02F 3/34*** | (2023.01) |
| ***C12N 1/20*** | (2026.01) |
| ***C12R 1/38*** | (2006.01) |
| *C02F 101/34* | (2006.01) |

(52) U.S. Cl.

CPC .............. *C02F 3/341* (2013.01); *C02F 3/106* (2013.01); *C02F 3/107* (2013.01); *C02F 3/108* (2013.01); *C02F 3/12* (2013.01); *C12N 1/20* (2013.01); *C02F 2101/34* (2013.01); *C02F 2103/38* (2013.01); *C12R 2001/38* (2021.05)

(58) Field of Classification Search

CPC ............. C02F 2103/38; C12R 2001/01; C12R 2001/38; Y02W 30/62

See application file for complete search history.

(56) References Cited

FOREIGN PATENT DOCUMENTS

| | | |
|---|---|---|
| JP | H1042864 A | 2/1998 |
| JP | 2008199957 A | 9/2008 |

OTHER PUBLICATIONS

Wu, Wenyang, et al. "Genome sequencing reveals mechanisms for heavy metal resistance and polycyclic aromatic hydrocarbon degradation in Delftia lacustris strain LZ-C." Ecotoxicology 25.1 (2016): 234-247. (Year: 2016).*

"CATTO" et al., "Bioremoval of graffiti using novel commercial strains of bacteria", Science of the Total Environment, 2021, vol. 756, No. 144075, pp. 1-13.

Shigematsu et al., "Delftia tsuruhatensis sp. nov., a terephthalate-assimilating bacterium isolated from activated sludge", International Journal of Systematic and Evolutionary Microbiology, 2003, vol. 53, pp. 1479-1483.

Supplemental European Search Report for Corresponding European Patent Application No. 22841937.0, Dec. 5, 2025, 14 pages.

Qiu et al., "Biodegradation of bis(2-hydroxyethyl) terephthalate by a newly isolated Enterobacter sp. HY1 and characterization of its esterase properties", J Basic Microbiol., 2020, vol. 60, pp. 699-711.

Yoshida et al., "A bacterium that degrades and assimilates poly-(ethylene terephthalate)", Science, 2016, vol. 351, Issue 6278, pp. 1196-1199.

Taniguchi et al., "Biodegradation of PET: Current Status and Application Aspects", ACS Catal., 2019, vol. 9, No. 5, pp. 4089-4105.

International Search Report for Corresponding International Patent Application No. PCT/JP2022/025831, 4 pages, Sep. 13, 2022.

Zhang et al., "Biodegradable PLA/PBAT mulch on microbial community structure in different soils", International Biodeterioration & Biodegradation, 2019, vol. 145, pp. 1-7.

Joo et al., "Structural insight into molecular mechanism of poly (ethylene terephthalate) degradation", Nature Communications, 2018, vol. 9: 382, pp. 1-12.

Roberts et al., "Environmental Consortium Containing *Pseudomonas* and *Bacillus* Species Synergistically Degrades Polyethylene Terephthalate Plastic", MSPHERE, 2020, vol. 5, No. 6, pp. 1-20.

Supplementary European Search Report for Corresponding European Patent Application No. 22841937.0, Apr. 10, 2026, 18 pages.

* cited by examiner

*Primary Examiner* — Bradley R Spies

(74) *Attorney, Agent, or Firm* — Lucas & Mercanti, LLP

(57) ABSTRACT

The invention provides a microorganism that can degrade aromatic polyester or a degradation product thereof and a method for degrading aromatic polyester or a degradation product thereof with the use of such microorganism. The microorganism is a bacterial strain that degrades aromatic polyester or a degradation product such as the strain No. 2a (Accession Number: NITE BP-03483); the strain No. 7a (Accession Number: NITE BP-03484); or the strain No. 8d (Accession Number: NITE BP-03485).

3 Claims, 24 Drawing Sheets

Specification includes a Sequence Listing.

Fig. 2-1

```
Query    1 ATTGAACGCTGGCGGCATGCCTTACACATGCAAGTCGAACGGTAACAGGTCTTCGGACGC  60
           ||||||||||||||||||||||||||||||||||||||||||||||||||||||||||||
Sbjct   20 ATTGAACGCTGGCGGCATGCCTTACACATGCAAGTCGAACGGTAACAGGTCTTCGGACGC  79

Query   61 TGACGAGTGGCGAACGGGTGAGTAATACATCGGAACGTGCCCAGTCGTGGGGGATAACTA 120
           ||||||||||||||||||||||||||||||||||||||||||||||||||||||||||||
Sbjct   80 TGACGAGTGGCGAACGGGTGAGTAATACATCGGAACGTGCCCAGTCGTGGGGGATAACTA 139

Query  121 CTCGAAAGAGTAGCTAATACCGCATACGATCTGAGGATGAAAGCGGGGGACCTTCGGGCC 180
           ||||||||||||||||||||||||||||||||||||||||||||||||||||||||||||
Sbjct  140 CTCGAAAGAGTAGCTAATACCGCATACGATCTGAGGATGAAAGCGGGGGACCTTCGGGCC 199

Query  181 TCGCGCGATTGGAGCGGCCGATGGCAGATTAGGTAGTTGGTGGGATAAAAGCTTACCAAG 240
           ||||||||||||||||||||||||||||||||||||||||||||||||||||||||||||
Sbjct  200 TCGCGCGATTGGAGCGGCCGATGGCAGATTAGGTAGTTGGTGGGATAAAAGCTTACCAAG 259

Query  241 CCGACGATCTGTAGCTGGTCTGAGAGGACGACCAGCCACACTGGGACTGAGACACGGCCC 300
           ||||||||||||||||||||||||||||||||||||||||||||||||||||||||||||
Sbjct  260 CCGACGATCTGTAGCTGGTCTGAGAGGACGACCAGCCACACTGGGACTGAGACACGGCCC 319

Query  301 AGACTCCTACGGGAGGCAGCAGTGGGGAATTTTGGACAATGGGCGAAAGCCTGATCCAGC 360
           ||||||||||||||||||||||||||||||||||||||||||||||||||||||||||||
Sbjct  320 AGACTCCTACGGGAGGCAGCAGTGGGGAATTTTGGACAATGGGCGAAAGCCTGATCCAGC 379

Query  361 AATGCCGCGTGCAGGATGAAGGCCTTCGGGTTGTAAACTGCTTTTGTACGGAACGAAAAA 420
           ||||||||||||||||||||||||||||||||||||||||||||||||||||||||||||
Sbjct  380 AATGCCGCGTGCAGGATGAAGGCCTTCGGGTTGTAAACTGCTTTTGTACGGAACGAAAAA 439

Query  421 GCTCCTTCTAATACAGGGGGCCCATGACGGTACCGTAAGAATAAGCACCGGCTAACTACG 480
           ||||||||||||||||||||||||||||||||||||||||||||||||||||||||||||
Sbjct  440 GCTCCTTCTAATACAGGGGGCCCATGACGGTACCGTAAGAATAAGCACCGGCTAACTACG 499

Query  481 TGCCAGCAGCCGCGGTAATACGTAGGGTGCGAGCGTTAATCGGAATTACTGGGCGTAAAG 540
           ||||||||||||||||||||||||||||||||||||||||||||||||||||||||||||
Sbjct  500 TGCCAGCAGCCGCGGTAATACGTAGGGTGCGAGCGTTAATCGGAATTACTGGGCGTAAAG 559

Query  541 CGTGCGCAGGCGGTTATGTAAGACAGATGTGAAATCCCCGGGCTCAACCTGGGAACTGCA 600
           ||||||||||||||||||||||||||||||||||||||||||||||||||||||||||||
Sbjct  560 CGTGCGCAGGCGGTTATGTAAGACAGATGTGAAATCCCCGGGCTCAACCTGGGAACTGCA 619

Query  601 TTTGTGACTGCATGGCTAGAGTACGGTAGAGGGGGATGGAATTCCGCGTGTAGCAGTGAA 660
           ||||||||||||||||||||||||||||||||||||||||||||||||||||||||||||
Sbjct  620 TTTGTGACTGCATGGCTAGAGTACGGTAGAGGGGGATGGAATTCCGCGTGTAGCAGTGAA 679

Query  661 ATGCGTAGATATGCGGAGGAACACCGATGGCGAAGGCAATCCCCTGGACCTGTACTGACG 720
           ||||||||||||||||||||||||||||||||||||||||||||||||||||||||||||
Sbjct  680 ATGCGTAGATATGCGGAGGAACACCGATGGCGAAGGCAATCCCCTGGACCTGTACTGACG 739
```

Fig. 2-2

```
Query   721 CTCATGCACGAAAGCGTGGGGAGCAAACAGGATTAGATACCCTGGTAGTCCACGCCCTAA  780
            ||||||||||||||||||||||||||||||||||||||||||||||||||||||||||||
Sbjct   740 CTCATGCACGAAAGCGTGGGGAGCAAACAGGATTAGATACCCTGGTAGTCCACGCCCTAA  799

Query   781 ACGATGTCAACTGGTTGTTGGGAATTAGTTTTCTCAGTAACGAAGCTAACGCGTGAAGTT  840
            ||||||||||||||||||||||||||||||||||||||||||||||||||||||||||||
Sbjct   800 ACGATGTCAACTGGTTGTTGGGAATTAGTTTTCTCAGTAACGAAGCTAACGCGTGAAGTT  859

Query   841 GACCGCCTGGGGAGTACGGCCGCAAGGTTGAAACTCAAAGGAATTGACGGGGACCCGCAC  900
            ||||||||||||||||||||||||||||||||||||||||||||||||||||||||||||
Sbjct   860 GACCGCCTGGGGAGTACGGCCGCAAGGTTGAAACTCAAAGGAATTGACGGGGACCCGCAC  919

Query   901 AAGCGGTGGATGATGTGGTTTAATTCGATGCAACGCGAAAAACCTTACCCACCTTTGACA  960
            ||||||||||||||||||||||||||||||||||||||||||||||||||||||||||||
Sbjct   920 AAGCGGTGGATGATGTGGTTTAATTCGATGCAACGCGAAAAACCTTACCCACCTTTGACA  979

Query   961 TGGCAGGAAGTTTCCAGAGATGGATTCGTGCTCGAAAGAGAACCTGCACACAGGTGCTGC 1020
            ||||||||||||||||||||||||||||||||||||||||||||||||||||||||||||
Sbjct   980 TGGCAGGAAGTTTCCAGAGATGGATTCGTGCTCGAAAGAGAACCTGCACACAGGTGCTGC 1039

Query  1021 ATGGCTGTCGTCAGCTCGTGTCGTGAGATGTTGGGTTAAGTCCCGCAACGAGCGCAACCC 1080
            ||||||||||||||||||||||||||||||||||||||||||||||||||||||||||||
Sbjct  1040 ATGGCTGTCGTCAGCTCGTGTCGTGAGATGTTGGGTTAAGTCCCGCAACGAGCGCAACCC 1099

Query  1081 TTGTCATTAGTTGCTACATTCAGTTGAGCACTCTAATGAGACTGCCGGTGACAAACCGGA 1140
            ||||||||||||||||||||||||||||||||||||||||||||||||||||||||||||
Sbjct  1100 TTGTCATTAGTTGCTACATTCAGTTGAGCACTCTAATGAGACTGCCGGTGACAAACCGGA 1159

Query  1141 GGAAGGTGGGGATGACGTCAAGTCCTCATGGCCCTTATAGGTGGGGCTACACACGTCATA 1200
            ||||||||||||||||||||||||||||||||||||||||||||||||||||||||||||
Sbjct  1160 GGAAGGTGGGGATGACGTCAAGTCCTCATGGCCCTTATAGGTGGGGCTACACACGTCATA 1219

Query  1201 CAATGGCTGGTACAGAGGGTTGCCAACCCGCGAGGGGGAGCTAATCCCATAAAACCAGTC 1260
            ||||||||||||||||||||||||||||||||||||||||||||||||||||||||||||
Sbjct  1220 CAATGGCTGGTACAGAGGGTTGCCAACCCGCGAGGGGGAGCTAATCCCATAAAACCAGTC 1279

Query  1261 GTAGTCCGGATCGCAGTCTGCAACTCGACTGCGTGAAGTCGGAATCGCTAGTAATCGCGG 1320
            ||||||||||||||||||||||||||||||||||||||||||||||||||||||||||||
Sbjct  1280 GTAGTCCGGATCGCAGTCTGCAACTCGACTGCGTGAAGTCGGAATCGCTAGTAATCGCGG 1339

Query  1321 ATCAGCATGCCGCGGTGAATACGTTCCCGGGTCTTGTACACACCGCCCGTCACACCATGG 1380
            ||||||||||||||||||||||||||||||||||||||||||||||||||||||||||||
Sbjct  1340 ATCAGCATGCCGCGGTGAATACGTTCCCGGGTCTTGTACACACCGCCCGTCACACCATGG 1399

Query  1381 GAGCGGGTCTCGCCAGAAGTAGGTAGCCTAACCGCAAGGAGGGCG-CTTACCACGGCGGG 1439
            ||||||||||||||||||||||||||||||||||||||||||||| ||||||||||||||
Sbjct  1400 GAGCGGGTCTCGCCAGAAGTAGGTAGCCTAACCGCAAGGAGGGCGCCTTACCACGGCGGG 1459

Query  1440 GTTCGTGACTGGGGTGAAG 1458
            |||||||||||||||||||
Sbjct  1460 GTTCGTGACTGGGGTGAAG 1478
```

Fig. 5

| Test item | | SIID31076-01 |
|---|---|---|
| Culture temperature (°C) | | 30 |
| Cell form | | Rod-shaped bacteria (0.6 - 0.8 × 1.0 - 1.5 μm) |
| Gram-staining | | - |
| Spore formation | | - |
| Motility | | + |
| Colony form | Medium | Nutrient agar |
| | Culture period (hr) | 72 |
| | Diameter | 5-8 mm |
| | Hue | Cream color |
| | Shape | Irregular form |
| | Protrusion | Flat |
| | Margin | Waved |
| | Surface form etc. | Coarse surface |
| | Clarity | Translucent |
| | Viscosity | Butter-like |
| Growth temperature test | 37 (°C) | + |
| | 45 (°C) | - |
| Catalase reaction | | + |
| Oxidase reaction | | + |
| Generation of acid/gas from glucose (acid generation/gas generation) | | -/- |
| O/F test (oxidation/fermentation) | | -/- |

+ : Positive; - : negative

Fig. 6

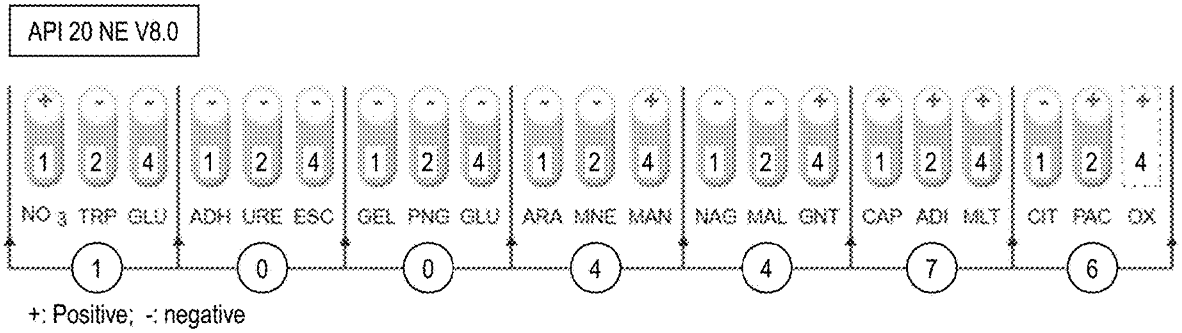

API20NE Description of items

| Test item | Reaction/enzyme | Test item | Reaction/enzyme |
|---|---|---|---|
| NO3 | Nitrate reduction* | MAN | D-mannitol** |
| TRP | Indole production* | NAG | N-acetyl-D-glucosamine** |
| GLU | Glucose oxidation* | MAL | Maltose** |
| ADH | Arginine dihydrolase* | GNT | Potassium gluconate** |
| URE | Urease* | CAP | n-capric acid** |
| ESC | Esculin hydrolysis* | ADI | Adipic acid** |
| GEL | Gelatin hydrolysis* | MLT | dl-malic acid** |
| PNPG | β-galactosidase* | CIT | Sodium citrate** |
| GLU | Glucose** | PAC | Phenyl acetate** |
| ARA | L-arabinose** | OX | Cytochrome oxidase* |
| MNE | D-mannose** | | |

*Biochemical test; **Assimilability test

Fig. 7

| Test item | Test result |
|---|---|
| Lipase activity (Tween 80) | + |
| Casein hydrolysis | + |
| Growth at 40°C | + |
| Salt resistance (NaCl) | |
| 4% | + |
| 5% | + |
| 6% | - |
| API ZYM | |
| Alkaline phosphatase | + |
| Esterase (C4) | + |
| Esterase/lipase (C8) | + |
| Lipase (C14) | - |
| Leucine aryl amidase | + |
| Valine aryl amidase | - |
| Cystine aryl amidase | - |
| Trypsin | - |
| Chymotrypsin | - |
| Acid phosphatase | + |
| Naphthol-AS-BI-phosphohydrolase | + |
| α-galactosidase | - |
| β-galactosidase | - |
| β-glucuronidase | - |
| α-glucosidase | - |
| β-glucosidase | - |
| *N*-acetyl-β-glucosaminidase | - |
| α-mannosidase | - |
| α-fucosidase | - |

+: Positive; -: negative

Fig. 11

| Test item | | SIID31076-02-B1 |
|---|---|---|
| Culture temperature (°C) | | 30 |
| Cell form | | Rod-coccus cycle of rod-shaped bacteria is observed<br>20 hr: 0.6 - 0.9 × 1.0 - 2.5 μm<br>72 hr: 0.7 × 0.8 μm |
| Gram-staining | | + |
| Spore formation | | - |
| Motility | | - |
| Colony form | Medium | Nutrient agar |
| | Culture period (hr) | 72 |
| | Diameter | 0.9-1.5 mm |
| | Hue | Cream color |
| | Shape | Round |
| | Protrusion | Lenticular |
| | Margin | Entire margin |
| | Surface form etc. | Smooth |
| | Clarity | Opaque |
| | Viscosity | Butter-like |
| Growth temperature test | 37 (°C) | +w |
| | 45 (°C) | - |
| Catalase reaction | | + |
| Oxidase reaction | | - |
| Generation of acid/gas from glucose (acid generation/gas generation) | | -/- |
| O/F test (oxidation/fermentation) | | -/- |

+ : Positive; - : negative; +w : weakly-reactive

Fig. 12

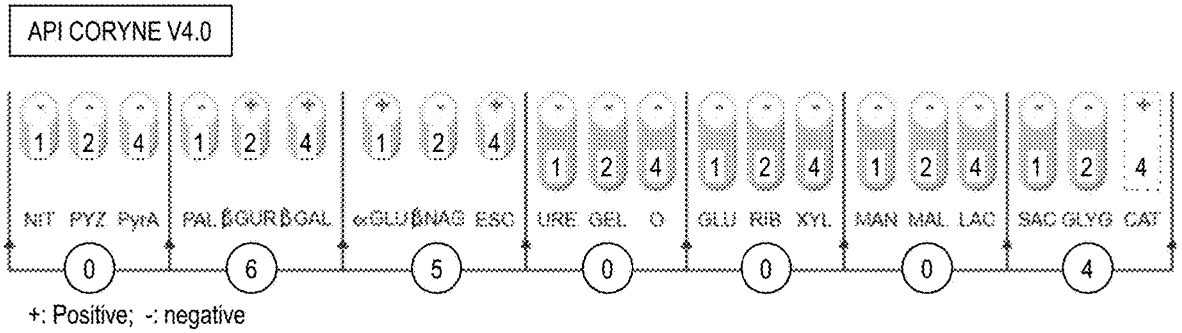

APICORYNE Description of items

| Test item | Reaction | Test item | Reaction |
|---|---|---|---|
| NIT | Nitrate reduction* | GEL | Gelatin hydrolysis* |
| PYZ | Pyrazinamidase* | GLU | Glucose** |
| PYRA | Pyrrolidonyl arylamidase* | RIB | Ribose** |
| PAL | Alkaline phosphatase* | XYL | Xylose** |
| βGUR | β-glucuronidase* | MAN | Mannitol** |
| βGAL | β-galactosidase* | MAL | Maltose** |
| αGLU | α-glucosidase* | LAC | Lactose** |
| βNAG | N-acetyl-β-glucosaminidase* | SAC | Sucrose** |
| ESC | Esculin (β-glucosidase)* | GLYG | Glycogen** |
| URE | Urease* | CAT | Catalase* |

0= Control、*Biochemical test; **Fermentability test

Fig. 13

| Test item | Test result |
| --- | --- |
| Casein hydrolysis | + |
| Tyrosine hydrolysis | + |
| Starch hydrolysis | - |
| Growth under anaerobic conditions | - |

+: Positive; -: negative

Fig. 17

| Test item | | SIID31076-03 |
|---|---|---|
| Culture temperature (°C) | | 30 |
| Cell form | | Rod-shaped bacteria (0.6 - 0.8 × 1.0 - 2.0 μm) |
| Gram-staining | | - |
| Spore formation | | - |
| Motility | | + |
| Colony form | Medium | Nutrient agar |
| | Culture period (hr) | 72 |
| | Diameter | 4-5 mm |
| | Hue | Cream color |
| | Shape | Irregula |
| | Protrusion | Flat |
| | Margin | Waved |
| | Surface form etc. | Smooth |
| | Clarity | Translucent |
| | Viscosity | Butter-like |
| Growth temperature test | 37 (°C) | + |
| | 45 (°C) | - |
| Catalase reaction | | + |
| Oxidase reaction | | + |
| Generation of acid/gas from glucose (acid generation/gas generation) | | -/- |
| O/F test (oxidation/fermentation) | | +/- |

+ : Positive; - : negative

Fig. 18

API 20 NE V8.0

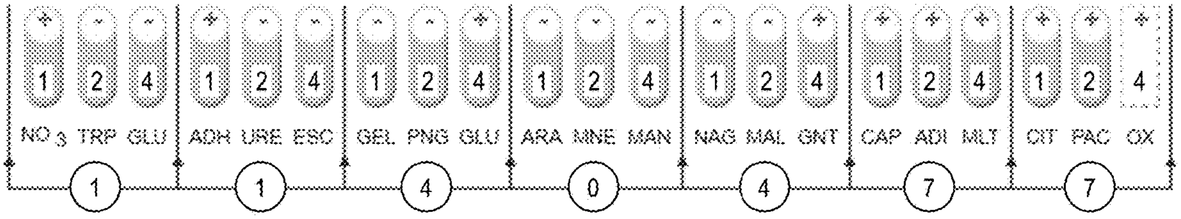

+: Positive; -: negative

API20NE Description of items

| Test item | Reaction/enzyme | Test item | Reaction/enzyme |
|---|---|---|---|
| NO3 | Nitrate reduction* | MAN | D-mannitol** |
| TRP | Indole production* | NAG | N-acetyl-D-glucosamine** |
| GLU | Glucose oxidation* | MAL | Maltose** |
| ADH | Arginine dihydrolase* | GNT | Potassium gluconate** |
| URE | Urease* | CAP | n-capric acid** |
| ESC | Esculin hydrolysis* | ADI | Adipic acid** |
| GEL | Gelatin hydrolysis* | MLT | dl-malic acid** |
| PNPG | β-Galactosidase* | CIT | Sodium citrate** |
| GLU | Glucose** | PAC | Phenyl acetate** |
| ARA | L-arabinose** | OX | Cytochrome oxidase* |
| MNE | D-m annose** | | |

*Biochemical test; **Assimilability test

Fig. 19

| Test item | Test result |
|---|---|
| Starch hydrolysis | - |
| Production of fluorescent dye on King's A and King's B agar media | - |

+: Positive; -: negative

AROMATIC POLYESTER-DEGRADING BACTERIA

CROSS-REFERENCE TO RELATED APPLICATIONS

This application is a 371 of PCT/JP2022/025831, filed Jun. 28, 2022, which claims the benefit of Japanese Patent Application No. 2021-115744, filed Jul. 13, 2021

REFERENCE TO A SEQUENCE LISTING SUBMITTED ELECTRONICALLY VIA EFS-WEB

The content of the electronically submitted sequence listing, file name: 522-1255_SequenceListing.txt; size: 8 KB; and date of creation: Jan. 12, 2024, filed herewith, is incorporated herein by reference in its entirety.

TECHNICAL FIELD

The present invention relates to a technique of rapidly degrading wastewater containing aromatic polyester, such as polyethylene terephthalate (PET), or a degradation product thereof using microorganisms.

BACKGROUND ART

While awareness of environmental issues is increasing, standards for industrial wastewater become tighter around the world. When constructing a new factory, for example, it is required to present an evidence demonstrating that wastewater treatment is performed according to the criteria. That is, wastewater treatment is recognized as a critical technique constituting a part of a production process in recent years. Polyethylene terephthalate (PET) that is used for beverage bottles or polyester fibers may generate wastewater in the production process or in the recycling process thereof. When such wastewater contains a PET degradation product at high concentration, it is difficult to sufficiently degrade such wastewater with existing active sludge. With the use of microorganisms that degrade aromatic polyester-binding compounds found in the present invention in combination with active sludge, the aforementioned problem can be dissolved.

For example, it was difficult to degrade, with existing active sludge, wastewater containing BHET discharged in the process of chemical recycling of PET. In such a case, the cost for factory operation would be influenced to a significant extent because of the necessity of outsourcing wastewater management by paying the cost therefor and coordination of operations.

While isolation of *Enterobacter* sp. as a microorganism that would degrade BHET had been reported, the extent of degradation of 200 mg/l (about 8 mM) of BHET thereby was as low as approximately 30% over a period of 120 hours (Non Patent Literature: 1).

CITATION LIST

Non Patent Literature

Non Patent Literature 1: Lequan Qiu et al., J. Basic Microbiol., 2020; 60:699-711

SUMMARY OF INVENTION

Technical Problem

The present invention provides microorganisms that can degrade aromatic polyester, or a degradation product thereof such as BHET, and a method for degrading aromatic polyester, or a degradation product thereof such as BHET, using such microorganisms.

Solution to Problem

The present inventors had conducted concentrated studies on a method for treating wastewater containing aromatic polyester, such as polyethylene terephthalate (PET), or a degradation product thereof, such as wastewater containing BHET discharged in the process of PET recycling. As a result, the present inventors discovered microorganisms that would rapidly degrade BHET from soil and they also discovered that such microorganisms would efficiently degrade BHET. In addition, they discovered that use of such microorganisms by themselves or in combination with active sludge would enable rapid treatment of wastewater containing BHET, which was difficult to degrade in the past. This has led to the completion of the present invention.

Specifically, the present invention is as described below.

[1] A microorganism that degrades aromatic polyester or a degradation product thereof selected from among the 3 bacterial strains indicated below:
- (i) the *Delftia lacustris* strain;
- (ii) the *Pseudarthrobacter* sp. strain of the genus *Pseudarthrobacter*; or
- (iii) the *Pseudomonas* sp. strain of the genus *Pseudomonas*.

[2] The microorganism that degrades aromatic polyester or a degradation product thereof selected from among the 3 bacterial strains indicated below:
- (i) the strain No. 2a (Accession Number: NITE BP-03483), which is the *Delftia lacustris* strain;
- (ii) the strain No. 7a (Accession Number: NITE BP-03484), which is the *Pseudarthrobacter* sp. strain of the genus *Pseudarthrobacter*: or
- (iii) the strain No. 8d (Accession Number: NITE BP-03485), which is the *Pseudomonas* sp. strain of the genus *Pseudomonas*.

[3] The microorganism according to [1] or [2], which degrades bis(2-hydroxyethyl) terephthalate (BHET).

[4] The microorganism according to [1] or [2], which degrades monohydroxyethyl terephthalate (MHET).

[5] The microorganism according to [1] or [2], which degrades terephthalic acid (TPA).

[6] A method for degrading aromatic polyester or a degradation product thereof comprising bringing at least one of the microorganism according to any of [1] to [3] into contact with aromatic polyester or a degradation product thereof.

[7] The method according to [6], which comprises degrading aromatic polyester or a degradation product thereof in wastewater generated in the process of polyethylene terephthalate (PET) recycling.

[8] The method according to [6] or [7], wherein the aromatic polyester or a degradation product thereof is bis(2-hydroxyethyl) terephthalate (BHET).

[9] A composition comprising at least one of the microorganism according to any of [1] to [5].

[10] The composition according to [9], which is active sludge.

[11] The composition according to [9], which is a carrier for microorganisms that supports the microorganism according to any of [1] to [5] thereon.

[12] The composition according to [11], wherein the carrier for microorganisms is selected from the group consisting of resin, active carbon, and zeolite.

[13] A method for degrading aromatic polyester or a degradation product thereof in a waste generated in the process of PET recycling comprising bringing the composition according to any of [9] to into contact with wastewater generated in the process of polyethylene terephthalate (PET) recycling.

[14] The method according to [13], wherein the aromatic polyester or a degradation product thereof is bis(2-hydroxyethyl) terephthalate (BHET).

The description incorporates the contents disclosed by JP Patent Application No. 2021-115744, based on which the priority of the present application claims.

Advantageous Effects of Invention

Use of the microorganism that can degrade aromatic polyester, or a degradation product thereof such as BHET, according to the present invention enables chemical recycling of PET to be performed smoothly. Use of such microorganism by itself or in combination with active sludge would enable rapid treatment of wastewater containing BHET, which was difficult to degrade in the past.

BRIEF DESCRIPTION OF DRAWINGS

FIG. 1 shows the results of phylogenetic deduction based on the 16s rRNA nucleotide sequence of the strain 2a.

FIG. 2-1 shows the results of comparison of the partial 16S rDNA nucleotide sequences between the strain 2a and the *Delftia lacustris* strain.

FIG. 2-2 shows the results of comparison of the partial 16S rDNA nucleotide sequences between the strain 2a and the *Delftia lacustris* strain (a continuation from FIG. 2-1).

FIG. 3 shows a colony image of the strain 2a.

FIG. 5 shows the results of biochemical properties test of the strain 2a (the first-stage test of bacteria).

FIG. 6 shows the results of biochemical properties test of the strain 2a (the second-stage test of bacteria).

FIG. 7 shows the results of biochemical properties test of the strain 2a (the second-stage test of bacteria (additional test)).

FIG. 8 shows the results of phylogenetic deduction based on the 16S rDNA nucleotide sequence of the strain 7a.

FIG. 9 shows a colony image of the strain 7a.

FIG. 11 shows the results of biochemical properties test of the strain 7a (the first-stage test of bacteria).

FIG. 12 shows the results of biochemical properties test of the strain 7a (the second-stage test of bacteria).

FIG. 13 shows the results of biochemical properties test of the strain 7a (the second-stage test of bacteria (additional test)).

FIG. 17 shows the results of biochemical properties test of the strain 8d (the first-stage test of bacteria).

FIG. 18 shows the results of biochemical properties test of the strain 8d (the second-stage test of bacteria).

FIG. 19 shows the results of biochemical properties test of the strain 8d (the second-stage test of bacteria (additional test)).

FIG. 20A shows the results of the control, FIG. 20B shows the results of the strain 2a, FIG. 20C shows the results of the strain 7a, and FIG. 20D shows the results of the strain 8d.

FIG. 21A shows the results of the control, FIG. 21B shows the results of the strain 2a, FIG. 21C shows the results of the strain 7a, and FIG. 2D shows the results of the strain 8d.

FIG. 22A shows the results of the control, FIG. 22 Bshows the results of the strain 2a, FIG. 22C shows the results of the strain 7a, and FIG. 22D shows the results of the strain 8d.

FIG. 23A shows the results of the control, FIG. 23B shows the results of the strain 2a, FIG. 23C shows the results of the strain 7a, and FIG. 23D shows the results of the strain 8d.

DESCRIPTION OF EMBODIMENTS

Figure 1:
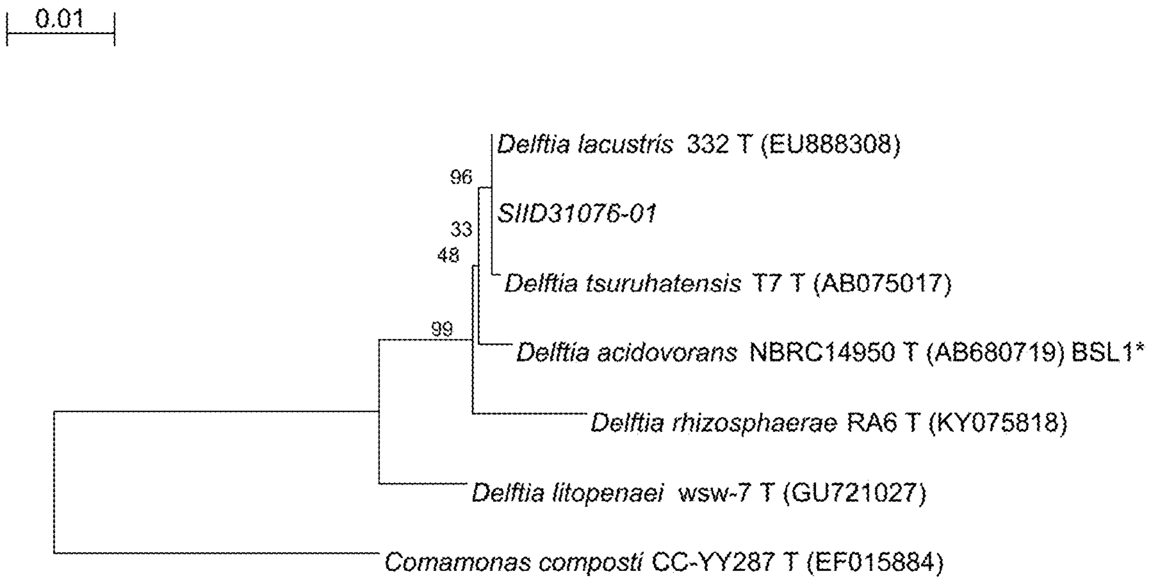

Hereafter, the present invention is described in detail.

In the present invention, the symbol "%" indicating the concentration is by weight (wt %).

The microorganisms of the present invention are aromatic polyester-degrading bacteria that degrade aromatic polyester, such as polyethylene terephthalate (PET).

In the present invention, the term "polyester" refers to a polymeric substance containing ester bonds in its main chain. "Aromatic polyester" that is degraded by the microorganisms of the present invention is polyester comprising, as a repeat unit, an aromatic component. The content of the repeat unit is, for example, 50 to 100% by weight, preferably 70 to 100% by weight, more preferably 90 to 100% by weight, and further preferably 95 to 100% by weight, relative to the entire compound. An example of aromatic polyester is polyethylene terephthalate (PET), and another example is PET comprising 95% by weight or more ethylene terephthalate repeat units.

Aromatic polyester can be produced by polycondensation of a dicarboxylic acid component and a diol component. For example, aromatic polyester can be produced with the use of terephthalic acid as the dicarboxylic acid component of PET and ethylene glycol as the diol component thereof. Examples of dicarboxylic acid components other than terephthalic acid include: aromatic dicarboxylic acids, such as phthalic acid, isophthalic acid, diphenyldicarboxylic acid, diphenoxyethane dicarboxylic acid, and 2,5-naphthalene dicarboxylic acid, and derivatives thereof; and aliphatic dicarboxylic acids, such as succinic acid, adipic acid, azelaic acid, sebacic acid, and decane dicarboxylic acid, and derivatives thereof. Examples of diol components other than ethylene glycol include diethylene glycol, trimethylene glycol, tetramethylene glycol, propylene glycol, pentamethylene glycol, hexamethylene glycol, and decamethylene glycol.

When degrading aromatic polyester with the use of the aromatic polyester-degrading bacteria of the present invention, the form of the aromatic polyester to be degraded is not particularly limited. Examples thereof include fibrous, particulate, flaky, pellet, film, aggregated, and bottle forms. Alternatively, a composite of any thereof can be used.

Microorganisms, which are the aromatic polyester-degrading bacteria of the present invention, can also degrade intermediate products of PET degradation: i.e., monohydroxyethyl terephthalate (MHET) and terephthalic acid (TPA). MHET is hydrolyzed to TPA, and TPA is degraded into carbon dioxide in the end. Specifically, BHET is degraded into MHET, MHET is degraded into TPA, and TPA is then degraded into carbon dioxide. Use of the microorganisms of the present invention enables complete degradation of intermediate products of PET degradation; i.e., BHET and MHET, into carbon dioxide in the end.

Microorganisms, which are the aromatic polyester-degrading bacteria of the present invention, degrade, in particular, bis(2-hydroxyethyl) terephthalate (BHET), which is an intermediate product of degradation and is discharged in wastewater at the time of chemical degradation and chemical recycling of polyethylene terephthalate (PET). The aromatic polyester-degrading bacteria of the present invention may be referred to as BHET-degrading bacteria.

PET may generate wastewater in the process of production or recycling thereof, and such wastewater contains a PET degradation product at high concentration. The microorganisms of the present invention can degrade such PET degradation products.

At the time of chemical recycling of PET, for example, PET is chemically degraded into a BHET monomer, purified, and repolymerized to prepare PET. Examples of methods for chemical degradation of PET include methanolysis, glycolysis, and hydrolysis. In the methods of recycling, BHET is discharged into wastewater, which is a waste.

Use of the microorganisms of the present invention enables degradation of BHET in wastewater, which is generated in the process of PET recycling.

Examples of the microorganisms of the present invention that can degrade aromatic polyester, such as BHET, or a degradation product thereof include the strain 2a, the strain 7a (31076-02-B1), and the strain 8d. These 3 bacterial strains are isolated from soil.

As a result of the identification test in respect of biochemical and genetic properties, the strain 2a was identified as the *Delftia lacustris* strain, the strain 7a (31076-02-B1) was identified as the *Pseudarthrobacter* sp. strain of the genus *Pseudarthrobacter*, and the strain 8d was identified as the *Pseudomonas* sp. strain of the genus *Pseudomonas*.

The Strain 2a: the *Delftia Lacustris Strain*

The 16S rDNA nucleotide sequence is shown in SEQ ID NO: 1. The highest homology thereof to the known 16S rDNA (the 16S rRNA gene) nucleotide sequence is 99.9%. FIG. 1 shows the results of phylogenetic deduction on the basis of the 16S rDNA nucleotide sequence.

The strain 2a was deposited at the NITE Patent Microorganisms Depositary, the National Institute of Technology and Evaluation (NITE) (#122, 2-5-8 Kazusakamatari, Kisarazu-shi, Chiba, Japan) as of Jun. 17, 2021 under Accession Number NITE P-03483 (Identification: 31076-01). The above-identified strain was transferred from the national deposition to the international deposition (the date of transfer to the international deposition requested: May 27, 2022; Accession Number: NITE BP-03483).

The Strain 7a (31076-02-B1): the *Pseudarthrobacter* sp. Strain

The 16S rDNA nucleotide sequence is shown in SEQ ID NO: 2. The highest homology thereof to the known 16S rDNA nucleotide sequence is 99.4%. FIG. 2 shows the results of phylogenetic deduction on the basis of the 16S rDNA nucleotide sequence.

The strain 7a (31076-02-B1) was deposited at the NITE Patent Microorganisms Depositary, the National Institute of Technology and Evaluation (NITE) (#122, 2-5-8 Kazusakamatari, Kisarazu-shi, Chiba, Japan) as of Jun. 17, 2021 under Accession Number NITE P-03484 (Identification: 1076-02-B1). The above-identified strain was transferred from the national deposition to the international deposition (the date of transfer to the international deposition requested: May 27, 2022: Accession Number: NITE BP-03484).

The strain 8d: *Pseudomonas* sp.

Figure 3:

The 16S rDNA nucleotide sequence is shown in SEQ ID NO: 3. The highest homology thereof to the known 16S rDNA nucleotide sequence is 99.7%. FIG. 3 shows the results of phylogenetic deduction on the basis of the 16S rDNA nucleotide sequence.

The strain 8d was deposited at the NITE Patent Microorganisms Depositary, the National Institute of Technology and Evaluation (NITE) (#122, 2-5-8 Kazusakamatari, Kisarazu-shi, Chiba, Japan) as of Jun. 17, 2021 under Accession Number NITE P-03485 (Identification: 31076-03). The above-identified strain was transferred from the national deposition to the international deposition (the date of transfer to the international deposition requested: May 27, 2022; Accession Number: NITE BP-03485).

The microorganisms of the present invention can be cultured with the use of any medium that allows the microorganisms to proliferate and is suitable for degradation of aromatic polyester, such as BHET, or a degradation product thereof. Examples of such medium include, but are not limited to, nutrient agar medium, MS medium, and MS(+) medium. A nutrient agar medium can be prepared by dissolving, for example, 5.0 g of meat extract, 10.0 g of peptone, 5.0 g of sodium chloride, and 15.0 g of agar in 1,000 ml of deionized water. A MS(+) medium comprises, for example, yeast extract, ammonium sulfate, and phosphate buffer, and it further comprises metal salt, such as iron sulfate, copper sulfate, zinc sulfate, manganese sulfate, or magnesium sulfate, and a hydrate thereof.

The microorganisms of the present invention may be cultured via static culture or shaking culture under aerobic conditions. Culture is preferably performed via static culture. In the case of shaking culture, the shaking speed is, for example, 100 to 400 reciprocations per minute, and preferably 200 to 300 reciprocations per minute.

The microorganisms of the present invention can be cultured at any temperature without limitation. For example, culture can be performed at 20° C. to 40° C., preferably at 25° C. to 35° C., and more preferably at 30° C. Culture can be performed at any pH level, and, for example, culture can be performed in a pH range of 5 to 9, and preferably in a pH range of 6 to 8. In order to adjust a pH level within the aforementioned range, inorganic acid, such as hydrochloric acid or sulfuric acid, inorganic base, such as sodium hydroxide or potassium hydroxide, an aqueous solution of any thereof, or a buffer, such as a phosphate buffer, may be used.

A culture period is not particularly limited. For example, a culture period can be for 1 day or longer, preferably 2 days or longer, more preferably 5 days or longer, and further preferably 10 days or longer to 5 months or shorter, preferably 2 months or shorter, and more preferably 1 month or shorter. During culture, it may be effective to add fresh microbial cells or exchange the medium with a fresh medium, according to need.

The present invention includes a method for degrading BHET with the use of a single type of the microorganisms or two or more types thereof in combination.

When the microorganisms are used to degrade BHET, the BHET-degrading ability can be determined by mixing BHET with the microorganisms and measuring OD600 of BHET in the treatment solution. Alternatively, BHET can be analyzed by means of, for example, thin-layer chromatography (TLC) or high-performance liquid chromatography (HPLC).

Aromatic polyester, such as BHET, or a degradation product thereof can be degraded by the microorganisms by bringing the microorganisms into contact with the aromatic polyester, such as BHET, or a degradation product thereof. When the microorganisms are brought into contact with the aromatic polyester, such as BHET, or a degradation product thereof, the aromatic polyester, such as BHET, or a degradation product thereof is mixed with the microorganisms, the microorganisms are allowed to react with the aromatic polyester, such as BHET, or a degradation product thereof, and the microorganisms are allowed to induce the degradation reaction of the aromatic polyester, such as BHET, or a degradation product thereof. The density of the microorganisms that are allowed to react at the time of degradation can be adequately determined in accordance with, for example, the amount of the aromatic polyester, such as BHET, to be degraded or a degradation product thereof. A reaction is performed at temperature of 20° C. to 40° C., preferably at 25° C. to 35° C., and further preferably at 30° C. A reaction is performed at a pH level around 7.0, preferably at 5.0 to 9.0, further preferably at 6.0 to 8.0, and particularly preferably at 6.5 to 7.5. A reaction period can be adequately determined in accordance with, for example, the amount of aromatic polyester, such as BHET, to be degraded or a degradation product thereof. A reaction period is for several hours to several months. When the treatment is performed for a long period of time, the microorganisms may be added at regular intervals.

Among the microorganisms described above, any single type of strain may be used, two types of strains: i.e., the strain 2a and the strain 7a (31076-02-B1), the strain 2a and the strain 8d, or the strain 7a (31076-02-B1) and the strain 8d, may be used in combination, or three types of strains: i.e., the strain 2a, the strain 7a (31076-02-B1), and the strain 8d, may be used in combination. When a single type of strain is used, conditions adequate for proliferation of the strain to be used and/or degradation of aromatic polyester, such as BHET, or a degradation product thereof can be determined more easily.

Among the three types of strains, the strain 8d exhibits the highest degrading ability. When 2 mM BHET, MHET, and TPA are treated with one platinum loopful of the microorganisms, in addition to BHET, MHET and TPA can be completely degraded within 24 hours. The strain 7a can completely degrade BHET within 24 hours and MHET within 96 hours. The strain 2a can almost completely degrade BHET, MHET, and PTA within 72 hours.

When degrading BHET with the use of the microorganisms of the present invention, the BHET concentration is 20 mM or lower, preferably 16 mM or lower, and further preferably 8 mM or lower. With the use of the microorganisms of the present invention, specifically, 8 mM BHET can be completely degraded within 72 hours, preferably within 48 hours, and further preferably within 24 hours. The microorganisms may be added to a solution containing BHET to degrade BHET.

The microorganisms of the present invention are used for treatment of wastewater containing aromatic polyester or a degradation product thereof such as BHET. The microorganisms of the present invention are preferably used for treatment of wastewater containing BHET generated in the process of chemical recycling of PET. In the process of chemical recycling of PET, PET is depolymerized with the use of ethylene glycol to produce an intermediate: i.e., BHET. Subsequently, a process of purification (distillation and recrystallization) is performed to obtain high-purity BHET. Wastewater discharged in the process of recrystallization contains, in addition to BHET, related substances, such as MHET and TPA, at high concentration.

A solution containing the microorganisms of the present invention is added to and brought into contact with the wastewater. Thus, aromatic polyester or a degradation product thereof such as BHET can be degraded.

In general, active sludge is used for treatment of a waste. The term "active sludge" used herein is a generic term indicating "live" and free-floating organic sludge containing aerobic microorganisms that are artificially and/or industrially cultured and grown. Active sludge is extensively used as a means for purifying discharged water and contaminated water in, for example, sewage treatment plants, night soil disposal plants, and water-purifier tanks. With the use of active sludge, however, it is impossible to degrade aromatic polyester or a degradation product thereof such as BHET. That is, a waste generated in the process of PET recycling and treated with active sludge still contains aromatic polyester or a degradation product thereof such as BHET.

In order to overcome the problem described above, the microorganisms of the present invention are mixed into active sludge, and wastewater, which is a waste generated in the process of PET recycling, is added to and mixed with active sludge containing the microorganisms of the present invention. Thus, aromatic polyester or a degradation product thereof such as BHET in the waste can be degraded.

To 1 liter of active sludge, for example, a culture solution of the microorganisms of the present invention may be added in an amount of approximately 1 to 100 ml, preferably 1 to 50 ml, and more preferably 5 to 10 ml, active sludge containing microorganisms may be added to wastewater containing BHET, and the resultant may then be treated at 20° C. to 40° C. for 8 hours to 7 days, preferably 8 hours to 3 days, more preferably 8 hours to 2 days, and further preferably 8 hours to 12 hours. The treated wastewater is released into a sea area as a treated sewage that would not exceed the environmental standards. The treated wastewater exceeding the environmental standards is disposed as an industrial waste.

In this case, a substance that serves for the nutrition of microorganisms, such as a medium, may be added to active sludge.

Before a waste generated in the process of PET recycling is mixed and treated with active sludge, the waste may be mixed with carriers that support other microorganisms of the present invention thereon and treated. An example of such carriers is resin carriers that can comprise microorganisms adhered thereto and supported thereon, and specific examples include resin, such as polyvinyl alcohol (PVA), polypropylene, or polyurethane, and a porous body with a large surface area, such as active carbon or zeolite. Examples of PVA carriers that can support microorganisms include Kuraray Poval™ and Kuragel® (Kuraray Co., Ltd.). Forms of carriers are not limited, and, for example, membrane-like carriers, capsule-like carriers, tube-like carriers, and gel-like carriers can be used. Carriers that can support microorganisms thereon are referred to as "carriers for microorganisms."

Also, wastewater generated in the process of PET recycling is introduced into a single-purpose incubator, the microorganisms of the present invention are proliferated by suspension culture, BHET is selectively degraded and removed from the wastewater, and organic substances other than BHET are removed from the remaining wastewater in an active sludge aeration tank. This process enables biochemical oxygen demand (BOD) removal and chemical oxygen demand (COD) removal.

In the foregoing description, a solution containing the microorganisms of the present invention, active sludge containing the microorganisms of the present invention, and carriers for microorganisms that support the microorganisms of the present invention thereon are each referred to as a composition comprising the microorganisms of the present invention.

The present invention also includes wastewater treatment facilities where wastewater generated in the process of PET recycling is treated as described above.

EXAMPLES

The present invention is described in greater detail with reference to the following examples, although the present invention is not limited to these examples.

[Example 1] Isolation and Activity Assay of BHET-Degrading Bacteria

1. Objective

In the process of chemical recycling of PET, PET is depolymerized with the use of ethylene glycol to produce an intermediate: i.e., BHET. Subsequently, a process of purification (distillation and recrystallization) is performed to obtain high-purity BHET. Wastewater discharged in the process of recrystallization contains, in addition to BHET, related substances, such as MHET and TPA, at high concentration. However, it was impossible to sufficiently treat such wastewater with the use of active sludge, and a novel technique of treatment had been awaited. Accordingly, an objective is to obtain bacteria that would efficiently degrade BHET.

2. Material and Method of Experiment 2.1: Soil Sample, Purified BHET, and Crystallized Wastewater Soil samples were obtained from the premise of the JEPLAN, INC. plant in Kawasaki. As a BHET reagent, a purified BHET pellet produced from recycling provided by JEPLAN, INC. was used. Of the three types of crystallized wastewater samples also provided by JEPLAN, INC. (Wastewater A 20190604, Wastewater B 20191009, and Wastewater C 20190517), Wastewater A was mainly used for experimentation.

2.2: Enrichment Culture Medium and Culture Method

Ten types of soil samples (1 g each) were suspended in 10 ml of physiological saline and allowed to stand at room temperature for 1 hour.

Enrichment culture was performed with the addition of 0.5 ml of the supernatant of the soil suspension to 10 ml of a screening medium containing BHET powders grounded in a mortar at 0.2% (8 mM) (0.2% BHET/MS (+)) (Table 1). Culture was performed with the use of a test tube (¢ 20 mm) at 30° C.

During enrichment culture, 0.1 ml of the culture solution was transferred into a fresh medium every week, and this procedure was repeated several times.

TABLE 1

| 0.2% BHET/MS(+) | | Trace elements |
|---|---|---|
| 0.02% | Yeast extract | 0.10% $FeSO_4 \cdot 7H_2O$ |
| 0.2% | Ammonium sulfate | 0.10% $MgSO_4 \cdot 7H_2O$ |
| 1% | Trace elements | 0.01% $CuSO_4 \cdot 5H_2O$ |
| 10 mM | Sodium phosphate buffer (pH 7.0) | 0.01% $MnSO_4 \cdot 5H_2O$ |
| | | 0.01% $ZnSO_4 \cdot 7H_2O$ |

2.3: Isolation of Bacteria

Bacteria were isolated from the culture solution containing the cultured bacteria by the plate dilution method. The culture solution was diluted to $10^3$- to $10^9$-fold with physiological saline, the resultant was applied to a 0.2% BHET/MS(+) agar medium (Table 2) and to a 0.2% BHET/MS(+1/10) agar medium in which the amount of the yeast extract was reduced to one-tenth of the former medium (Table 3), and plate culture was then performed at 30° C.

TABLE 2

| 0.2% BHET/MS(+) agar medium | |
|---|---|
| 0.02% | Yeast extract |
| 0.2% | Ammonium sulfate |
| 1% | Trace elements |
| 10 mM | Sodium phosphate buffer (pH 7.0) |
| 0.2% | BHET powder |
| 1.5% | Agar |

The composition of trace elements is as shown in Table 1.

TABLE 3

| 0.2% BHET/MS(+1/10) agar medium | |
|---|---|
| 0.002% | Yeast extract |
| 0.2% | Ammonium sulfate |
| 1% | Trace elements |
| 10 mM | Sodium phosphate buffer (pH 7.0) |
| 0.2% | BHET powder |
| 1.5% | Agar |

The composition of trace elements is as shown in Table 1.

2.4: Assay of BHET-Degrading Activity of Isolated Bacteria by HPLC Analysis

In order to inspect the BHET-degrading activity of the isolated bacteria, one platinum loopful of the bacteria that have been subcultured in the 0.2% BHET/MS(+) agar medium was extracted, inoculated in 10 ml of the 2 mM BHET/MS(+) medium, and shaking-cultured at 30° C. for 5 days. Thereafter, the culture solution was analyzed by HPLC.

A mobile phase (formic acid:acetonitrile:water=1:2:7, volume ratio) was added to 1 ml of the sampled culture solution to obtain an adequate dilution, followed by thorough agitation. The resultant was filtered through an amphipathic prefilter (0.20 μm) for pretreatment and was then analyzed by HPLC.

HPLC analysis was performed with the use of the apparatus (LC-2010A HT, Shimadzu Corporation) and columns (COSMOCIL $5C_{18}$-AR-II (4.5 I.D.×250 mm) and $5C_{18}$-AR-II Guard Columns, Nacalai Tesque, Inc.).

HPLC analysis was performed in an isocratic elution mode at the flow rate of the mobile phase (formic acid: acetonitrile:water=1:2:7, volume ratio) of 1 ml/min and column temperature of 40° C., and detection was performed at 254 nm. On the basis of the elution time, the peaks of BHET, MHET, and TPA in the culture solution were identified, and the peak areas thereof were inspected. Concerning BHET, the calibration curve showing the BHET concentration and the peak area was prepared with the use of an aqueous solution of BHET dissolved at 70° C., and quantitativeness thereof was also examined.

3. Results 3.1: Isolation of BHET-Assimilating Bacteria

The 3 bacterial strains shown below were separated by plate culture.

Strain 2a

Strain 7a (31076-02-B1)

Strain 8d

The bacterial strains were each identified at TechnoSuruga Laboratory Co., Ltd. The results of identification are shown below. The results of identification include the results of 16s rDNA nucleotide sequence analysis, the results of morphological observation, and the results of physiological/biochemical properties test (the first-stage test of bacteria and the second-stage test of bacteria).

3.2: Identification of Separated Microorganisms (1) Method of Identification (i) Culture Conditions Medium: Nutrient agar (Oxoid, GBR)

Culture temperature: 30° C.

Culture period: 24 to 72 hours

Other conditions: Aerobic culture (ii) Partial 16s rDNA Nucleotide Sequence Analysis DNA extraction: Achromopeptidase (FUJIFILM Wako Pure Chemical, Japan)

PCR amplification: Tks Gflex DNA Polymerase (Takara Bio, Japan)

Cycle sequence: BigDye Terminator v3.1 Cycle Sequencing Kit (Applied Biosystems, USA)

Primers used (Yasuyoshi Nakagawa et al., Method of gene analysis, Determination of the 16S rRNA gene nucleotide sequence, Society for Actinomycetes Japan (ed.), Classification and Identification of Actinomycetes, the Business Center of Academic Societies of Japan, 2001, pp. 88-117)

PCR amplification: 9F, 1510R

Sequence (about 1,500 bp): 9F, 515F, 1099F, 536R, 926R, 1510R

Sequence: ABI PRISM 3130xL Genetic Analyzer System (Applied Biosystems)

Nucleotide sequence determination: ChromasPro 2.1 (Technelysium, AUS)

BLAST homology search

Analysis software: ENKI v3.2 (TechnoSuruga Laboratory, Japan)

Database: DB-BA15.0 (TechnoSuruga Laboratory), International Nucleotide Sequence Database (DDBJ/ENA (EMBL)/GenBank)

Simple molecular phylogenetic analysis

Phylogenetic deduction: Neighbor joining method

Model of nucleotide substitution: Kimura-2-parameter

Evaluation of phylogenetic tree reliability: Bootstrap method (repeated 1,000 times)

(iii) First-Stage Test of Bacteria

On the basis of colony observation under a stereoscopic microscope, morphological observation under an optical microscope, and the method of Barrow & Feltham (Cowan and Steel's Manual for the Identification of Medical Bacteria, 3rd ed., Cambridge: Cambridge University Press, 1993), the catalase reaction, the oxidase reaction, acid/gas generation from glucose, and oxidation/fermentation (O/F) of glucose were tested.

Gram staining: Favor Nissui G (Nissui Pharmaceutical, Japan)

Microscope: Optical microscope BX50F4 (Olympus, Japan)

Stereoscopic microscope: SMZ800N (Nikon, Japan)

(iv) Second-Stage Test of Bacteria

The second-stage test of bacteria was performed with the kits indicated below.

The strain 2a: API 20 NE, API ZYM (bioMerieux, FRA)

The strain 7a: API CORYNE (bioMerieux, FRA)

The strain 8d: API 20 NE (bioMerieux, FRA)

(2) Results of Identification (i) Strain 2a

FIG. 1 shows the results of phylogenetic deduction on the basis of the 16S rDNA nucleotide sequence. In FIG. 1, a line in the upper-left part is a scale bar, a numerical value in the branch of the phylogenetic tree indicates a bootstrap value, T at the end of the strain name indicates a type strain of the species, and BSL indicates a biosafety level (BSL 1*(opportunistic pathogen) or higher is indicated). SEQ ID NO: 1 shows the 16s rDNA nucleotide sequence.

FIG. 2-1 and FIG. 2-2 (FIG. 2-2 is a continuation from FIG. 2-1) each show the results of comparison of the partial 16S rDNA nucleotide sequences between the strain 2a and the *Delftia lacustris* strain. In FIG. 2, "Query" shows the sequence of the strain 2a, and "Sbjct" shows the sequence of *Delftia lacustris.*

Figure 4:
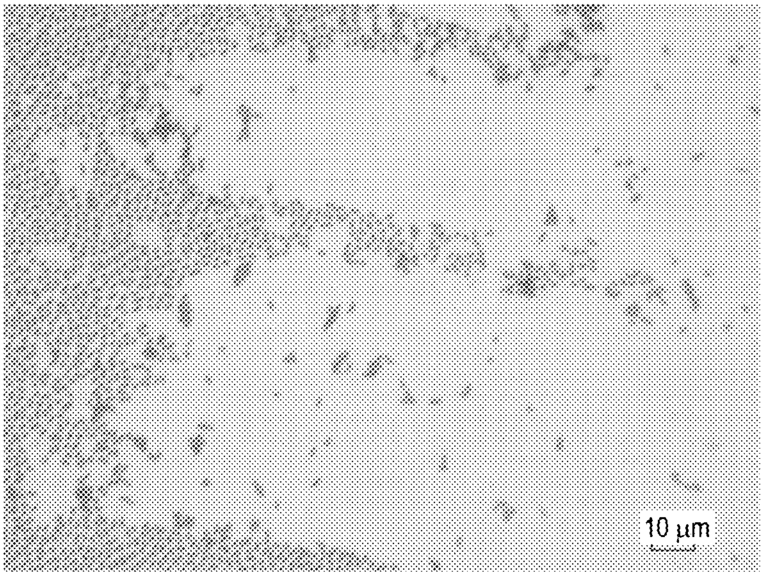
FIG. 4 shows a Gram-stained image of the 2a strain.

FIG. 3 shows a colony image of the strain 2a, and FIG. 4 shows a Gram-stained image of the 2a strain.

FIG. 5 shows biochemical properties (the results of the first-stage test of bacteria), FIG. 6 shows those (the results of the second-stage test of bacteria), and FIG. 7 shows those (the results of the second-stage test of bacteria (additional test)) of the strain 2a.

As a result of BLAST homology search performed with the use of DB-BA using the microorganism identification system "ENKI" and the international nucleotide sequence database, the partial 16S rDNA nucleotide sequence of the strain 2a was found to exhibit homology of 99.9% to the *Delftia lacustris* type strain 332T (Accession number EU888308) and *D. tsuruhatensis* T7T (AB075017).

The molecular phylogenetic tree analyzed based on the nucleotide sequence obtained by homology search using DB-BA (FIG. 1) demonstrates that the strain 2a is included in the cluster formed of *Delftia* and it is in the molecular phylogenetic position identical to that of *D. lacustris* 332T (EU888308).

As a result of the first-stage test of bacteria, the strain 2a was found to be a Gram-negative rod-shaped bacterium having motility, which did not oxidize glucose and show positive reactivity to catalase and oxidase (FIGS. 3, 4, and 5). Such properties were consistent with those of *Delftia.*

The results of the second-stage test of bacteria performed with the use of the API kit demonstrate that the specimen reduced nitrate, it assimilated D-mannitol, potassium gluconate, n-capric acid, and the like, and it did not assimilate glucose, maltose, and the like (FIG. 6). The results of the additional test demonstrated that the specimen grew in 5% NaCl, it hydrolyzed casein, and it exhibited lipase activity (Tween 80) (FIG. 7). FIG. 7 shows the results of enzyme reactions performed with the use of API ZYM. While such properties were found to be very similar to those of *D. lacustris*, differences were also observed therebetween. In particular, properties of the specimen were different from those of *D. lacustris* in that the specimen did not assimilate L-arabinose or N-acetyl-D-glucosamine and did not show α-glucosidase or β-glucuronidase activity.

On the basis of the results demonstrated above, the strain 2a was identified as the *D. lacustris* strain with a strong focus on the results of the partial 16S rDNA nucleotide sequence analysis.

The strain 2a was deposited at the NITE Patent Microorganisms Depositary, the National Institute of Technology and Evaluation (NITE) (#122, 2-5-8 Kazusakamatari, Kisarazu-shi, Chiba, Japan) as of Jun. 17, 2021 under Accession Number NITE P-03483 (Identification: 31076-01). The above-identified strain was transferred from the national deposition to the international deposition (the date of transfer to the international deposition requested: May 27, 2022; Accession Number: NITE BP-03483).

(ii) Strain 7a

Figure 8:
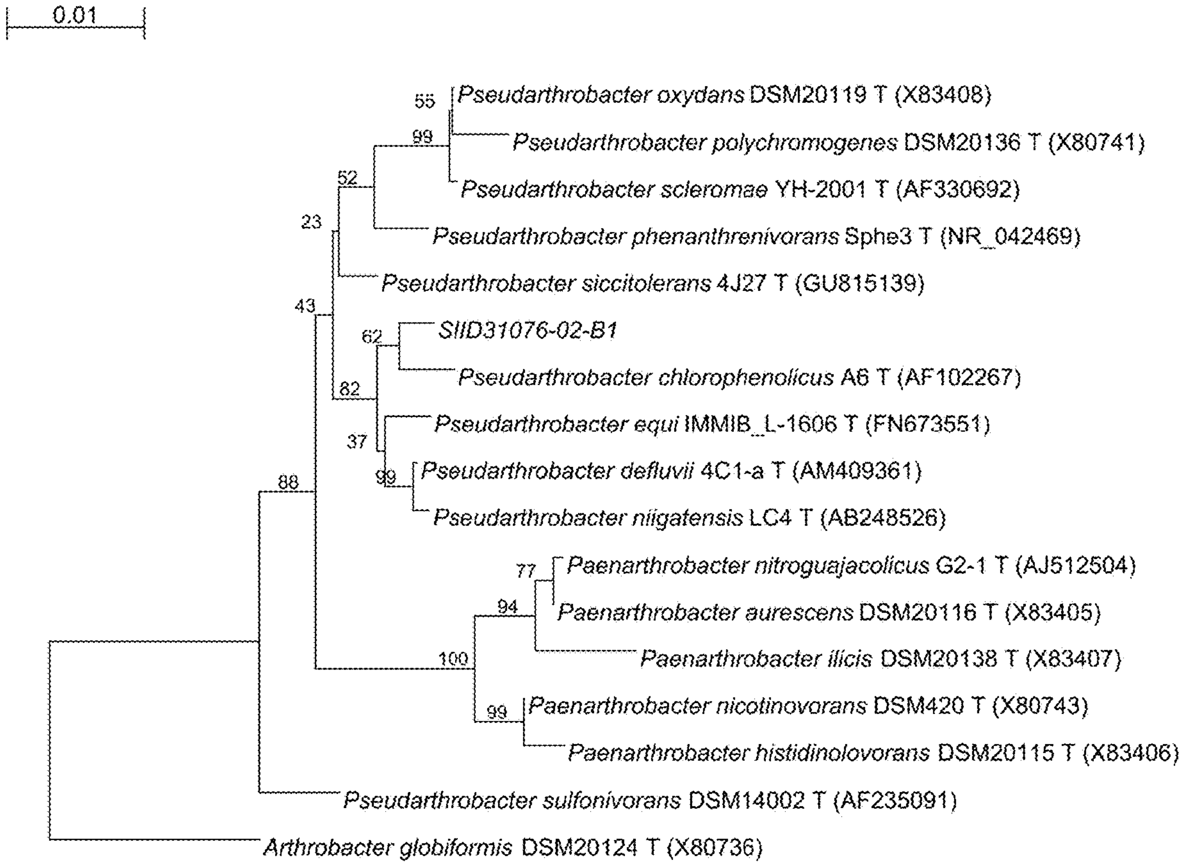

FIG. 8 shows the results of phylogenetic deduction on the basis of the 16S rDNA nucleotide sequence. In FIG. 8, a line in the upper-left part is a scale bar, a numerical value in the branch of the phylogenetic tree indicates a bootstrap value, T at the end of the strain name indicates a type strain of the species, and BSL indicates a biosafety level (BSL 1*(opportunistic pathogen) or higher is indicated). SEQ ID NO: 2 shows the 16s rDNA nucleotide sequence.

Figure 9:
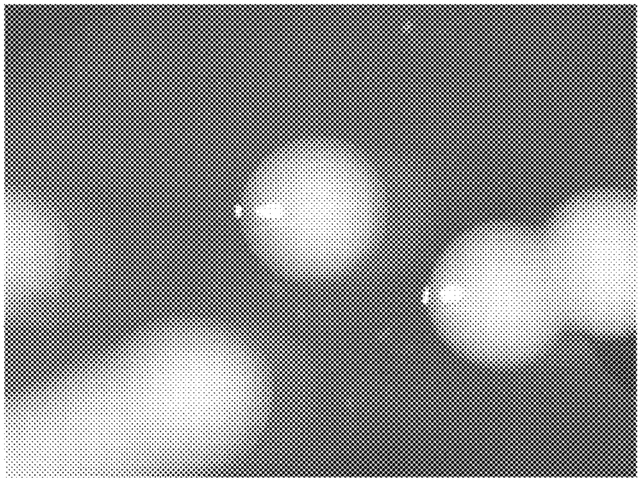
Figure 10:
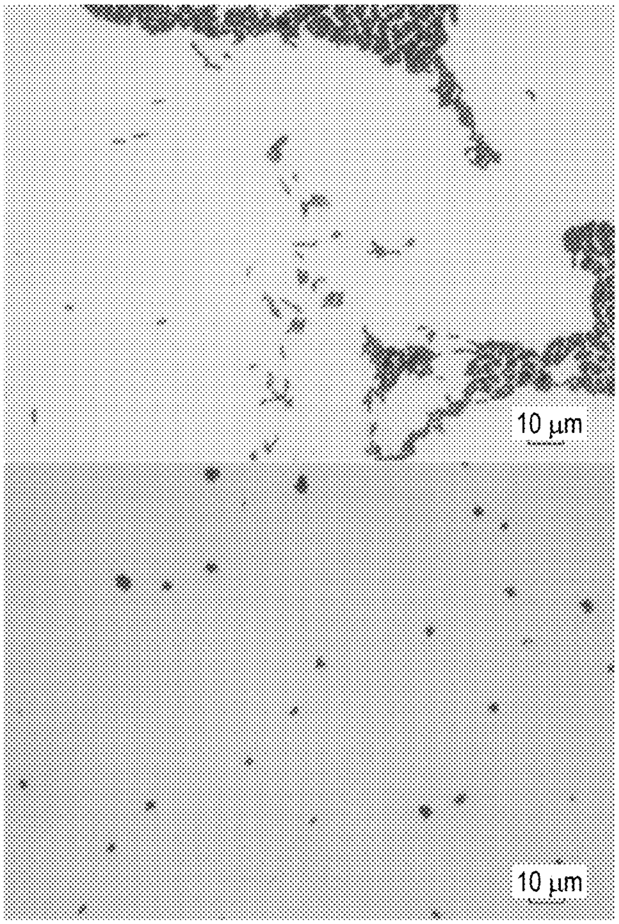
FIG. 10 shows a Gram-stained image of the 7a strain.

FIG. 9 shows a colony image of the strain 7a, and FIG. 10 shows a Gram-stained image of the 7a strain.

FIG. 11 shows biochemical properties (the results of the first-stage test of bacteria), FIG. 12 shows those (the results of the second-stage test of bacteria), and FIG. 13 shows those (the results of the second-stage test of bacteria (additional test)) of the strain 7a.

As a result of BLAST homology search performed with the use of DB-BA using the microorganism identification system "ENKI" and the international nucleotide sequence database, the partial 16S rDNA nucleotide sequence of SIID31076-02-B1 was found to exhibit homology of 99.4% to *Pseudarthrobacter equi* IMMIB L-1606T (FN673551), 99.1% to *P. defluvii* 4C1-aT (AM409361), and 99.0% to *P. chlorophenolicus* A6T (AF102267).

The molecular phylogenetic tree analyzed based on the nucleotide sequence obtained by homology search using DB-BA (FIG. 8) demonstrates that the strain 7a is included in the cluster formed of *Pseudarthrobacter* and it forms a cluster with *P. chlorophenolicus* A6T (AF102267), although the relationship therebetween seems to be distant.

As a result of the first-stage test of bacteria, the strain 7a was found to be a Gram-positive rod-shaped bacterium having no motility, which did not form spores and exhibited the rod-coccus life cycle in which an organism underwent morphological changes over the course of culture (FIGS. 9, 10, and 11). In addition, the results demonstrated that the strain 7a did not oxidize glucose, it showed positive reactivity to catalase, and it showed negative reactivity to oxidase (FIG. 11). Such properties were consistent with those of *Pseudarthrobacter.*

The results of the second-stage test of bacteria performed with the use of the API kit demonstrate that the specimen did not reduce nitrate, it hydrolyzed esculin, it did not hydrolyze gelatin, and it did not oxidize sugars (FIG. 12). The results of the additional test demonstrated that the specimen did not grow under anaerobic conditions, it hydrolyzed casein and tyrosine, but it did not hydrolyze starch (FIG. 13). While such properties were found to be similar to those of *P. chlorophenolicus* that had formed the same cluster in the results of partial 16S rDNA nucleotide sequence analysis, differences were also observed therebetween. In particular, properties of the specimen were different from those of *P. chlorophenolicus* in that the specimen did not exhibit motility and did not hydrolyze gelatin. No known species that were identical to the specimens were observed in known strains of *Pseudarthrobacter.*

The above results demonstrate that the strain 7a is of *Pseudarthrobacter* and, among known species, *P. chlorophenolicus* is most related thereto. However, the results of 16S rDNA nucleotide sequence analysis and physiological/biochemical properties test indicate that the strain 7a is different from *P. chlorophenolicus.*

In the end, the strain 7a was identified to be *Pseudarthrobacter* sp.

The strain 7a was deposited at the NITE Patent Microorganisms Depositary, the National Institute of Technology and Evaluation (NITE) (#122, 2-5-8 Kazusakamatari, Kisarazu-shi, Chiba, Japan) as of Jun. 17, 2021 under Accession Number NITE P-03484 (Identification: 31076-02-B1). The above-identified strain was transferred from the national deposition to the international deposition (the date of transfer to the international deposition requested: May 27, 2022: Accession Number: NITE BP-03484).

(iii) Strain 8d

Figure 14:
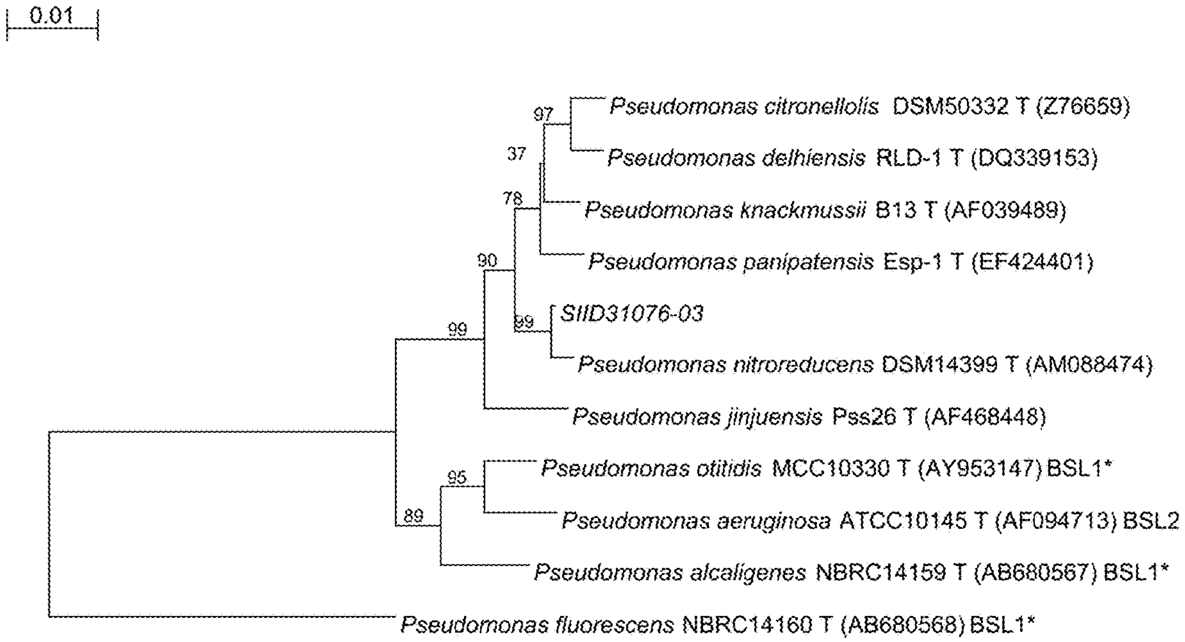
FIG. 14 shows the results of phylogenetic deduction based on the 16S rDNA nucleotide sequence of the strain 8d.

FIG. 14 shows the results of phylogenetic deduction on the basis of the 16S rDNA nucleotide sequence. In FIG. 14, a line in the upper-left part is a scale bar, a numerical value in the branch of the phylogenetic tree indicates a bootstrap value, T at the end of the strain name indicates a type strain of the species, and BSL indicates a biosafety level (BSL 1*(opportunistic pathogen) or higher is indicated). SEQ ID NO: 3 shows the 16s rDNA nucleotide sequence.

Figure 15:
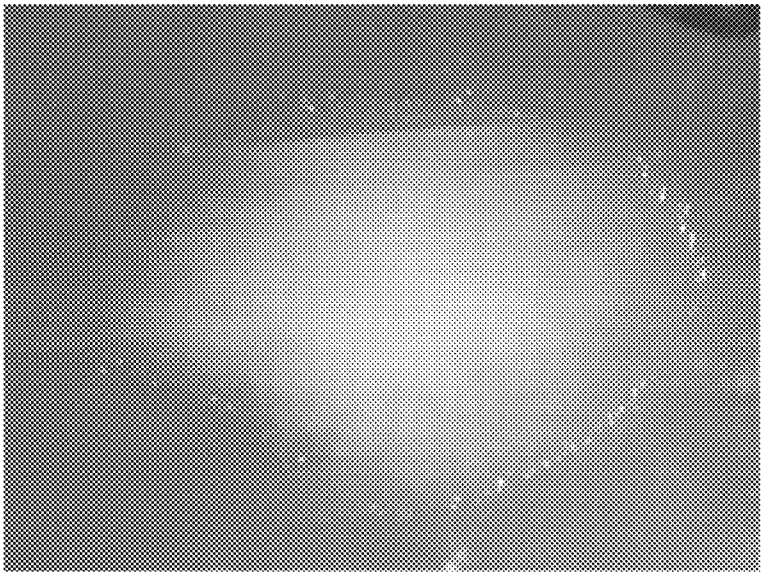
FIG. 15 shows a colony image of the strain 8d.
Figure 16:
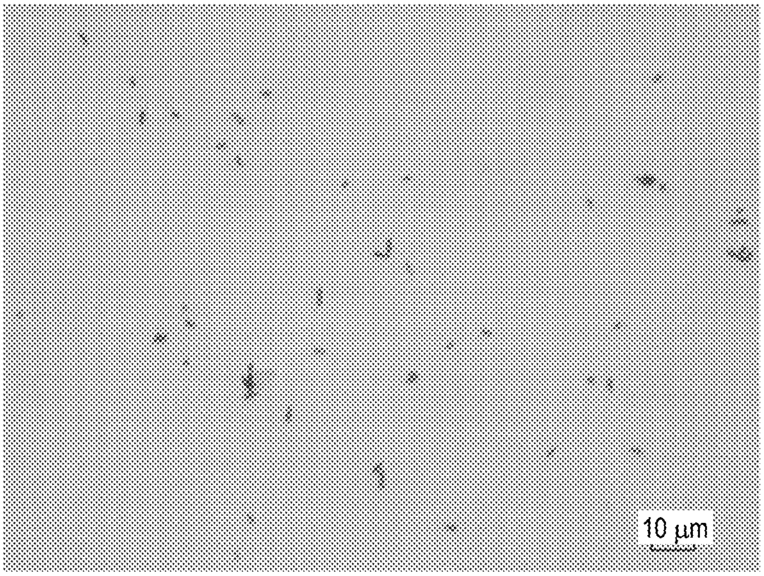
FIG. 16 shows a Gram-stained image of the 8d strain.

FIG. 15 shows a colony image of the strain 8d, and FIG. 16 shows a Gram-stained image of the 8d strain.

FIG. 17 shows biochemical properties (the results of the first-stage test of bacteria), FIG. 18 shows those (the results of the second-stage test of bacteria), and FIG. 19 shows those (the results of the second-stage test of bacteria (additional test)) of the strain 8d.

As a result of BLAST homology search performed with the use of DB-BA using the microorganism identification system "ENKI" and the international nucleotide sequence database, the partial 16S rDNA nucleotide sequence of the strain 8d was found to exhibit homology of 99.7% to *Pseudomonas nitroreducens* DSM 14399T (AM088474).

The molecular phylogenetic tree analyzed based on the nucleotide sequence obtained by homology search using DB-BA (FIG. 14) demonstrates that the strain 8d is included in the cluster formed of *Pseudomonas*, the strain 8d forms a cluster with *P. nitroreducens* DSM 14399T (AM088474), which is supported by a high bootstrap value of 99%, and the strain 8d is related to *P. nitroreducens* DSM 14399T (AM088474), although the relationship therebetween seems to be distant.

As a result of the first-stage test of bacteria, the strain 8d was found to be a Gram-negative rod-shaped bacterium having motility, which oxidized glucose and showed positive reactivity to both catalase and oxidase (FIGS. 15, 16, and 17). Such properties were consistent with those of *Pseudomonas.*

The results of the second-stage test of bacteria performed with the use of the API kit demonstrate that the specimen reduced nitrate, it exhibited arginine dihydrolase activity, it did not hydrolyze gelatin, it assimilated glucose, potassium gluconate, n-capric acid, and the like, and it did not assimilate L-arabinose, D-mannose, and the like (FIG. 18). The results of the additional test demonstrated that the specimen did not produce fluorescent dye on King's A and King's B agar media and it did not hydrolyze starch (FIG. 19). While such properties were found to be similar to but inconsistent with those of *P. nitroreducens* that had formed the same cluster as a result of partial 16S rDNA nucleotide sequence analysis. In particular, the specimen did not produce fluorescent dye and was different from *P. nitroreducens* in this respect.

The above results demonstrate that the strain 8d is of *Pseudomonas* and, among known species, *P. nitroreducens* is most related thereto. However, the results of 16S rDNA nucleotide sequence analysis and physiological/biochemical properties test indicate that the strain 8d is different from *P. nitroreducens*.

In the end, the strain 8d was identified to be *Pseudomonas* sp.

The strain 8d was deposited at the NITE Patent Microorganisms Depositary, the National Institute of Technology and Evaluation (NITE) (#122, 2-5-8 Kazusakamatari, Kisarazu-shi, Chiba, Japan) as of Jun. 17, 2021 under Accession Number NITE P-03485 (Identification: 31076-03). The above-identified strain was transferred from the national deposition to the international deposition (the date of transfer to the international deposition requested: May 27, 2022: Accession Number: NITE BP-03485).

3.3: Assay of Degrading Ability of BHET-Degrading Bacteria Over Time

Three different degrading bacteria (strains 2a, 7a, and 8d) were cultured in 2 mM BHET/MS(+) media. The culture solutions were sampled in an amount of 1 ml each every 24 hours, OD 600 was measured, and the culture solutions were then collected. The amount of BHET degraded was then inspected by HPLC.

While the BHET-degrading rate of the strain 2a was slower than that of the strain 7a or 8d, BHET, MHET, and TPA had substantially disappeared within 72 hours.

The strain 7a completely degraded BHET within 24 hours and it completely degraded MHET within 96 hours.

The strain 8d completely degraded BHET, MHET, and TPA within 24 hours.

The molecular weight of BHET is 254. Accordingly, 1 mM BHET is 254 mg/l BHET: i.e., 0.0254% BHET, and 8 mM BHET is 2032 mg/l BHET: i.e., 0.2032% BHET.

3.4: Activity of Degrading BHET at High Concentration

When actually treating crystallized wastewater, whether or not the strains 2a, 7a, and 8d would degrade BHET was examined with the use of culture solutions each containing 8 mM, 12 mM, and 16 mM BHET, in order to inspect as to the ability to degrade BHET at higher concentration. A culture solution of a similar composition, which was not supplemented with BHET-degrading bacteria, was used as a comparative standard.

BHET at a concentration of 8 mM or higher is not dissolved at 70° C., and it is thus impossible to sterilize such BHET by filtration. It is impossible to prepare a medium in the same manner as in the case of the BHET/MS(+) FT medium. Accordingly, a medium was prepared in the manner described below, although a small amount of BHET was degraded into MHET, disadvantageously. That is, BHET pellets were introduced into water to 16 mM, 24 mM, and 32 mM and completely dissolved by autoclave sterilization. Before BHET was deposited in an aqueous solution, the solution was mixed with the equivalent amount of 2×MS(+), which had also been subjected to autoclave sterilization, agitated, and dispensed into culture test tubes immediately thereafter.

To the 8 mM, 12 mM, or 16 mM BHET/MS(+) medium prepared, one platinum loopful of bacteria was suspended in 1 ml of MS(+) medium, and 80 μl each of the suspension was then inoculated in 10 ml each of the medium. Shaking culture was performed at 30° C., the culture solutions were sampled in an amount of 1 ml each every 24 hours, and the sampled culture solutions were stored at −20° C. The stored culture solutions were thawed on a later date, pH levels of the culture solutions were inspected, and the amount of BHET degraded was inspected by HPLC. The experiment was performed at n=2.

On the basis of the conditions of the culture solution 4 days after the initiation of culture, the strains 2a and 7a were found to proliferate at a BHET concentration of 16 mM. The strain 8d was not found to proliferate at a BHET concentration of 12 mM or higher.

Figure 20:
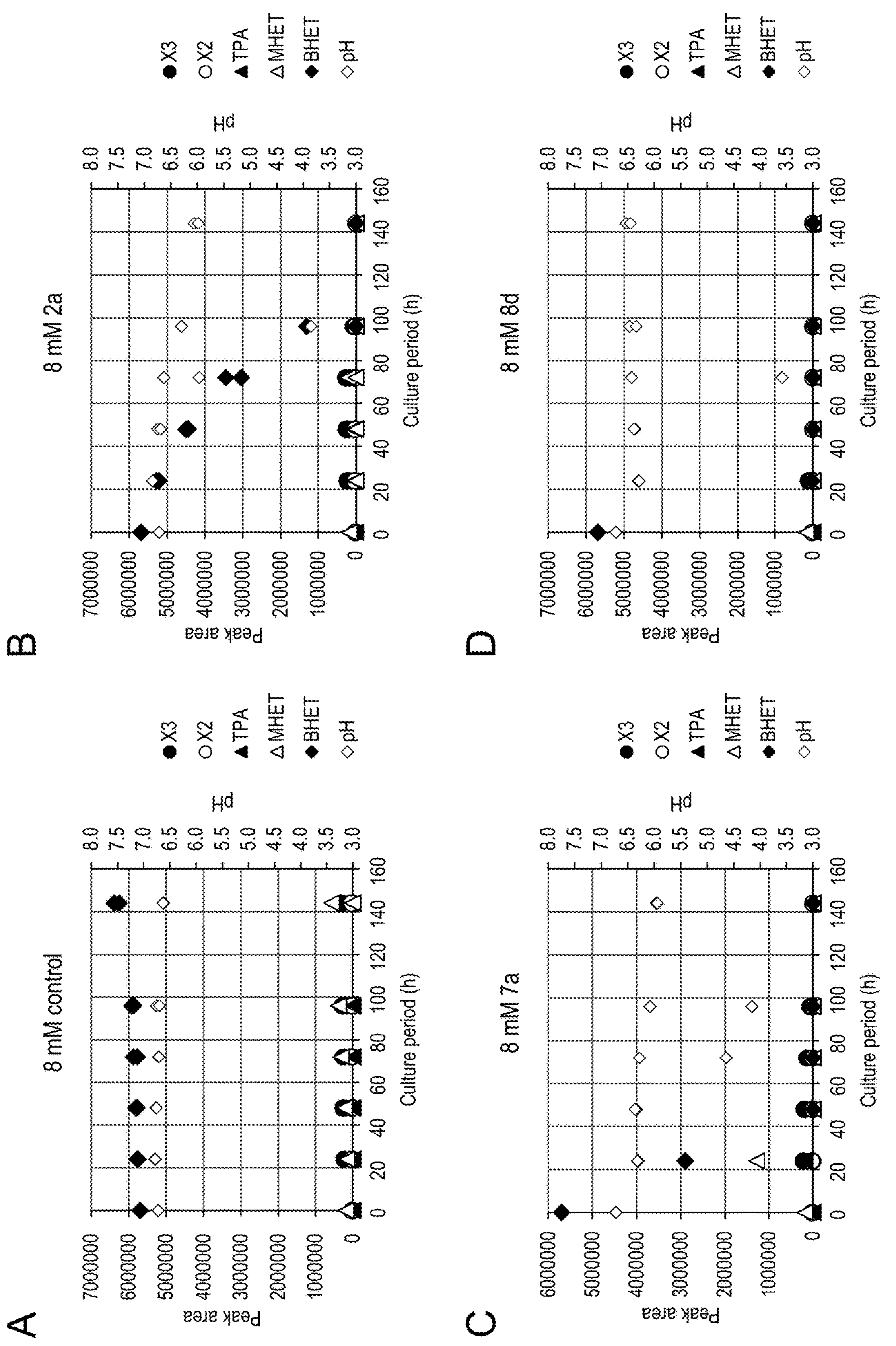
FIG. 20 shows degradation of 8 mM BHET by the strain 2a, the strain 7a, and the strain 8d over a period of 0 to 150 hours.
Figure 21:
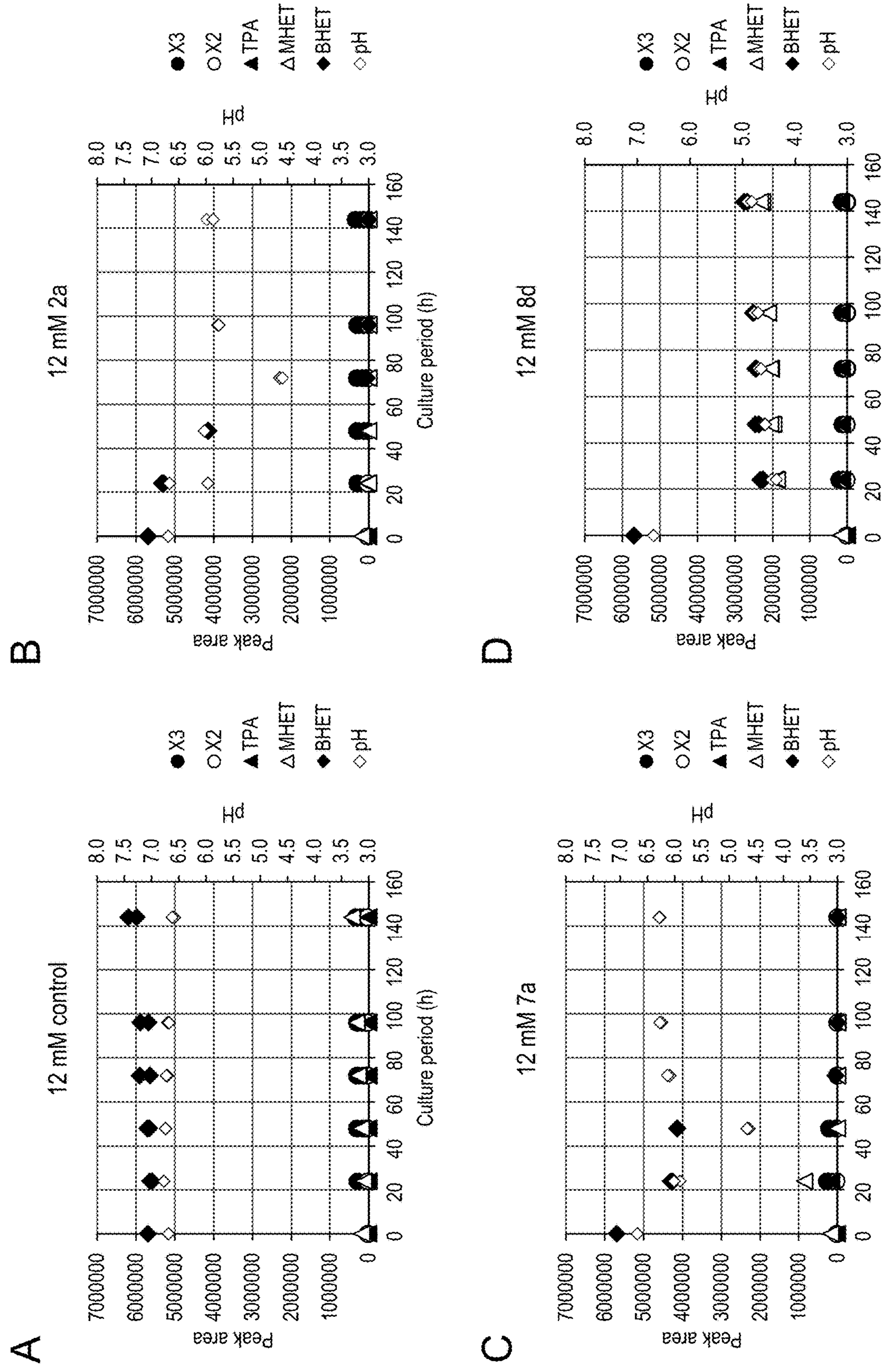
FIG. 21 shows degradation of 12 mM BHET by the strain 2a, the strain 7a, and the strain 8d over a period of 0 to 150 hours.
Figure 22:
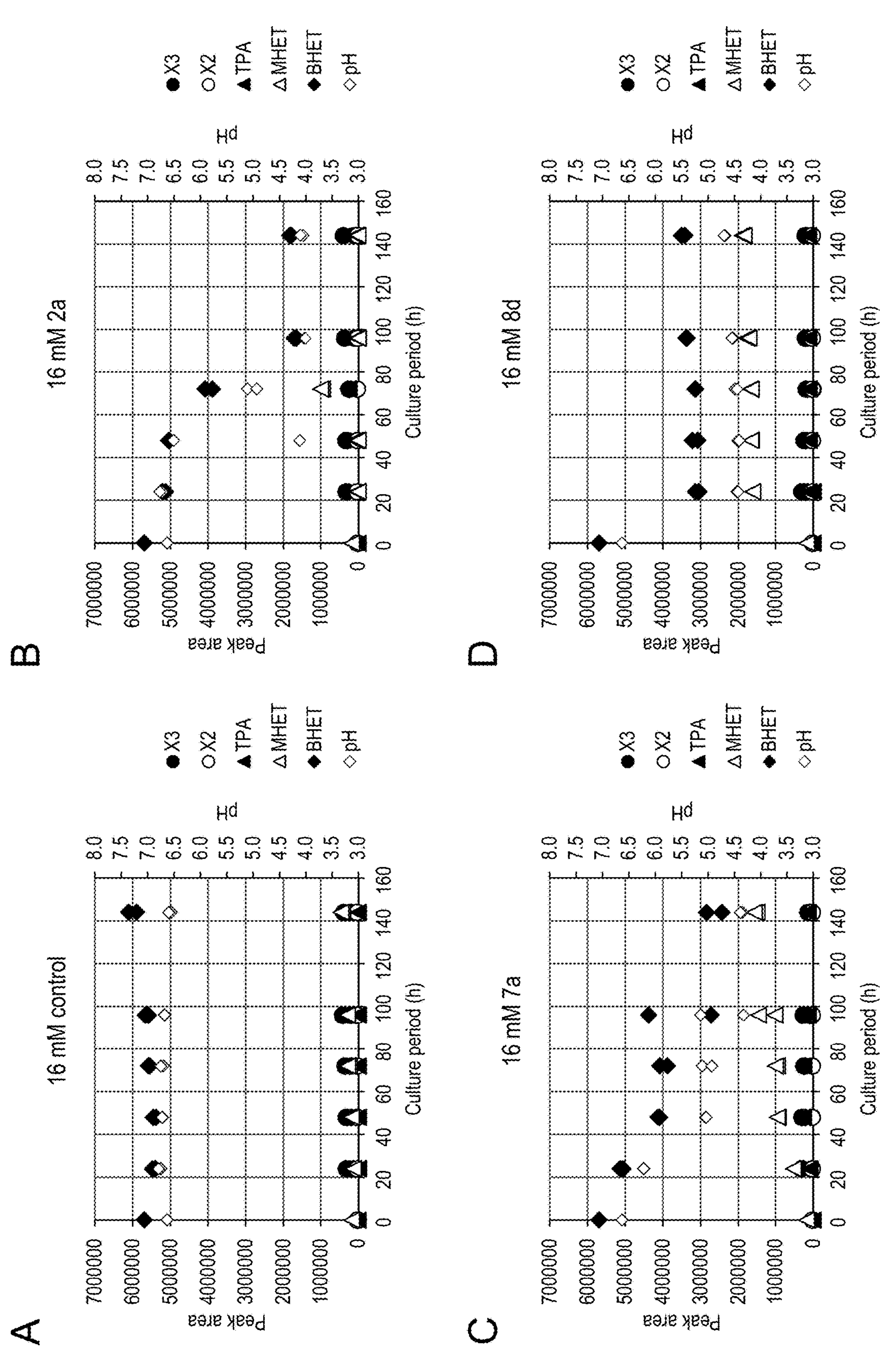
FIG. 22 shows degradation of 16 mM BHET by the strain 2a, the strain 7a, and the strain 8d over a period of 0 to 150 hours.

FIGS. 20 to 22 each show the results.

The strains 2a and 7a degraded 12 mM BHET within 3 days. The strain 2a exhibited the highest BHET-degrading activity at 12 mM, and the strain 7a exhibited the highest BHET-degrading activity at 8 mM. The strain 8d exhibited very high BHET-degrading activity at 8 mM and completely degraded BHET, MHET, and TPA within 24 hours.

[Example 2] Degradation of BHET in a Waste Generated in the Process of PET Recycling Performed With the Use of Active Sludge Containing BHET-Degrading Bacteria 1. Objective An objective is to verify an improvement in the BHET-degrading ability when the BHET-degrading bacteria isolated at Keio University are added to active sludge at wastewater treatment facilities of the JEPLAN, INC. plant.

2. Material and Method of Experiment 2.1: BHET-Degrading Bacteria, Purified BHET, and Active Sludge As the BHET-degrading bacteria, the three types of strains 2a, 7a, and 8d isolated at Keio University were used. The experiment was performed with the use of BHET produced by PET Refine Technology Co., Ltd., which is a subsidiary company of JEPLAN, INC., and active sludge sampled from wastewater treatment facilities of the JEPLAN, INC. Kitakyushu Hibikinada Plant.

2.2: Method of Experiment

To 5 ml of active sludge, 100 μl of a culture solution containing any of the 3 types of BHET-degrading bacteria was added, and a culture solution was prepared with the use of water as a solvent to bring the total amount of the solution to 10 ml with the addition of 1% of trace metals (Table 4) and 0.2 wt % of BHET. A culture solution of a similar composition, which was not supplemented with BHET-degrading bacteria, was used as a comparative standard. The prepared culture solution was shaking-cultured at 30° C., and 100 μl each of the samples were obtained 1 day, 2 days, 3 days, and 5 days after the initiation of culture.

TABLE 4

| Trace elements | |
|---|---|
| 0.10% | $FeSO_4 \cdot 7H_2O$ |
| 0.10% | $MgSO_4 \cdot 7H_2O$ |
| 0.01% | $CuSO_4 \cdot 5H_2O$ |
| 0.01% | $MnSO_4 \cdot 5H_2O$ |
| 0.01% | $ZnSO_4 \cdot 7H_2O$ |

2.3: Comparison of BHET-Degrading Activity by HPLC

A mobile phase (formic acid:acetonitrile:water=1:2:7, volume ratio) was added to 0.1 ml of the sampled culture solution to obtain a 10-fold dilution, followed by thorough agitation. The resultant was filtered through a 0.2-μm filter and was then analyzed by HPLC.

HPLC analysis was performed with the use of the apparatus (LC-2010A HT, Shimadzu Corporation) and columns (COSMOCIL $5C_{18}$-AR-II (4.6 I.D.×250 mm) and $5C_{18}$-AR-II Guard Columns, Nacalai Tesque, Inc.). HPLC analysis was performed in an isocratic elution mode at the flow rate of the mobile phase (formic acid:acetonitrile:water=1:2:7, volume ratio) of 1 ml/min and column temperature of 40° C., and detection was performed at 254 nm. On the basis of the elution time, the peaks of BHET, MHET, and TPA in the culture solution were identified, and the peak areas thereof were inspected. Concerning BHET, the calibration curve showing the BHET concentration and the peak area was prepared with the use of an aqueous solution of BHET dissolved at 70° C., and quantitativeness thereof was also examined.

3. Results

Three different types of BHET-degrading bacteria (the strains 2a, 7a, and 8d) were added to active sludge to prepare culture solutions, the culture solutions were sampled in an amount of 100 μl each 1 day, 2 days, 3 days, and 5 days immediately after the initiation of culture, and the amount of BHET degraded was inspected by HPLC.

Figure 23:
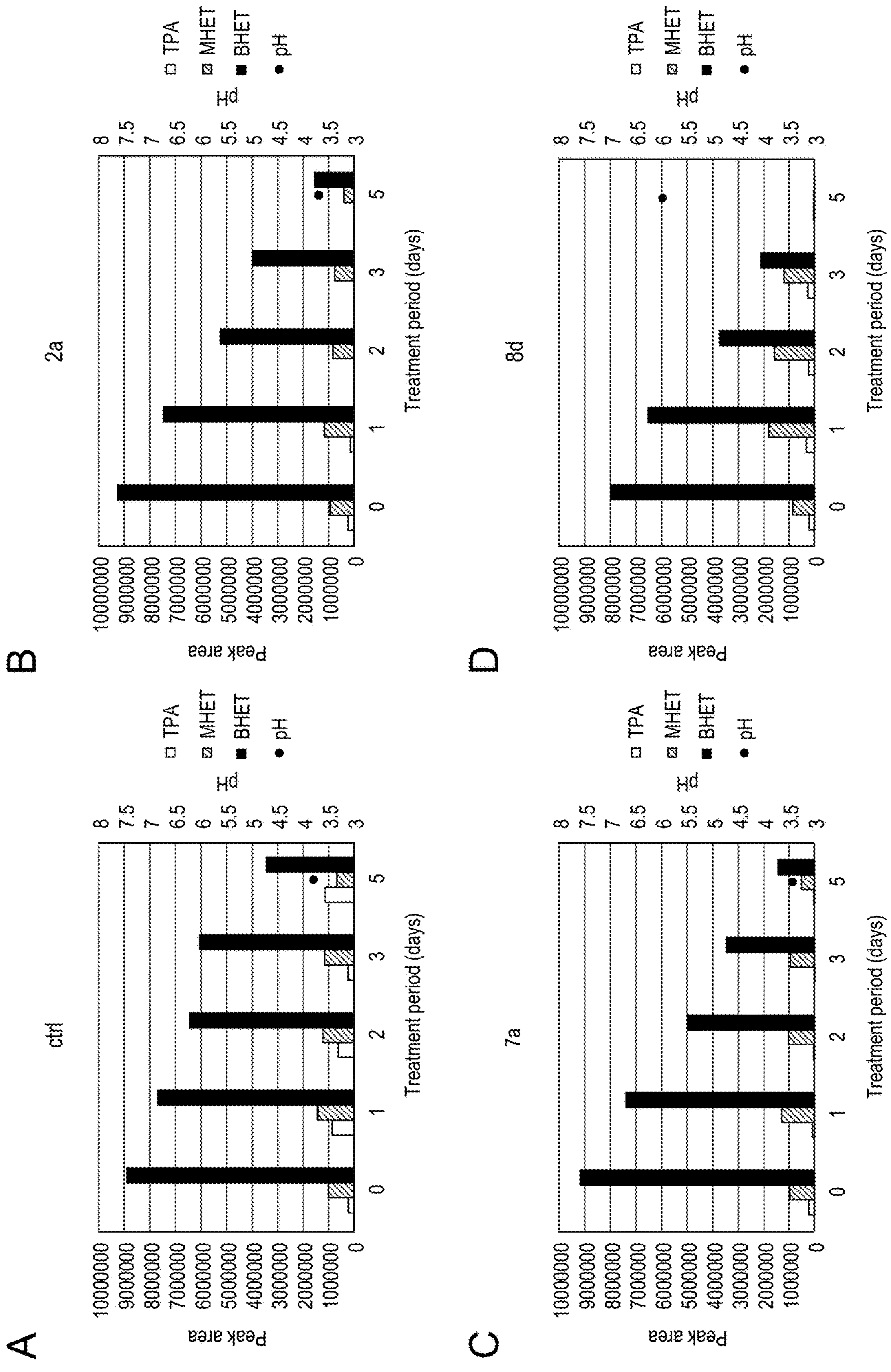
FIG. 23 shows degradation of BHET performed with the addition of the strain 2a, the strain 7a, and the strain 8d to active sludge.

FIG. 23 shows the results.

In comparison with the control sample consisting of active sludge, the BHET-degrading rates of the BHET-degrading bacterial strains 2a, 7a, and 8d were all improved. In particular, the BHET-degrading rate of the strain 8d was high, and BHET, MHET, and TPA had substantially disappeared 5 days later.

[Example 3] Degradation of BHET in a Waste Generated in the Process of PET Recycling Performed With the Use of BHET-Degrading Bacteria-Immobilized Carrier 1. Objective An objective is to verify the BHET-degrading ability when the BHET-degrading bacteria isolated at Keio University are immobilized on commercially available bacteria-immobilized carriers.

2. Material and Method of Experiment 2.1: BHET-Degrading Bacteria, Purified BHET, and Bacteria-Immobilized Carrier As the BHET-degrading bacteria, the strain 8d isolated at Keio University was used. The experiment was performed with the use of BHET produced by PET Refine Technology Co., Ltd., which is a subsidiary company of JEPLAN, INC. As a bacteria-immobilized carrier, PVA gel (Kuragel) (Kuraray Co., Ltd.) was used.

2.2: Immobilization of BHET-Degrading Bacteria on Bacteria-Immobilized Carrier

To a test tube, 5 ml of 0.4 wt % BHET and 5 ml of 2×MS(+) were added, and 100 μl of a culture solution of the BHET-degrading bacterial strain 8d was added thereto to prepare a culture solution. Kuragel (50 particles) substituted and washed with sterilized physiological saline was added thereto, and shaking culture was then performed at 30° C. for 2 days.

2.3: Method of Experiment

To a test tube, 5 ml of 0.4 wt % BHET and 5 ml of 2×MS(+) were added, and 50 particles of the BHET-degrading bacteria-immobilized carriers were added thereto to prepare a culture solution. The prepared culture solution was shaking-cultured at 30° C., and 100 μl of the sample was obtained 1 day later.

2.4: Comparison of BHET-Degrading Activity by HPLC

A mobile phase (formic acid:acetonitrile:water=1:2:7, volume ratio) was added to 0.1 ml of the sampled culture solution to obtain a 10-fold dilution, followed by thorough agitation. The resultant was filtered through a 0.2-μm filter and was then analyzed by HPLC.

HPLC analysis was performed with the use of the apparatus (LC-2010A HT, Shimadzu Corporation) and columns (COSMOCIL $5C_{18}$-AR-II (4.6 I.D.×250 mm) and $5C_{18}$-AR-II Guard Columns, Nacalai Tesque, Inc.). HPLC analysis was performed in an isocratic elution mode at the flow rate of the mobile phase (formic acid:acetonitrile:water=1:2:7, volume ratio) of 1 ml/min and column temperature of 40° C., and detection was performed at 254 nm. On the basis of the elution time, the peaks of BHET, MHET, and TPA in the culture solution were identified, and the peak areas thereof were inspected. Concerning BHET, the calibration curve showing the BHET concentration and the peak area was prepared with the use of an aqueous solution of BHET dissolved at 70° C., and quantitativeness thereof was also examined.

3. Results

Immediately after the culture solution of the BHET-degrading bacteria-immobilized carriers was prepared, 100 μl of the culture solution was sampled 1 day after the initiation of culture, and the amount of BHET degraded was inspected by HPLC.

The BHET-degrading rate of the BHET-degrading bacteria-immobilized carriers was high, and BHET, MHET, and TPA had substantially disappeared 1 day later.

INDUSTRIAL APPLICABILITY

With the use of the microorganisms of the present invention, polyethylene terephthalate can be recycled efficiently.

Accession Numbers

NITE BP-03483

NITE BP-03484

NITE BP-03485

All publications. patents. and patent applications cited herein are incorporated herein by reference in their entirety.

The invention claimed is:

1. A method for degrading bis(2-hydroxyethyl)terephthalate (BHET) comprising bringing at least one of the microorganisms that degrade aromatic polyester or a degradation product thereof selected from among the 2 bacterial strains indicated below:

(i) the *Pseudarthrobacter* sp. strain of the genus *Pseudarthrobacter*; or (ii) the *Pseudomonas* sp. strain of the genus *Pseudomonas*, into contact with bis(2-hydroxyethyl)terephthalate (BHET) or a degradation product thereof.

2. The method according to claim 1, which comprises degrading bis(2-hydroxyethyl)terephthalate (BHET) or a degradation product thereof in wastewater generated in the process of polyethylene terephthalate (PET) recycling.

3. The method according to claim 1, wherein the 2 bacterial strains are:

(i) the strain No. 7a (Accession Number: NITE BP-03484), which is the *Pseudarthrobacter* sp. strain of the genus *Pseudarthrobacter*; or (ii) the strain No. 8d (Accession Number: NITE BP-03485), which is the *Pseudomonas* sp. strain of the genus *Pseudomonas*.

* * * * *

SEQUENCE LISTING

```
<160> NUMBER OF SEQ ID NOS: 3

<210> SEQ ID NO 1
<211> LENGTH: 1458
<212> TYPE: DNA
<213> ORGANISM: Delftia lacustris
```

<400> SEQUENCE: 1
attgaacgct ggcggcatgc cttacacatg caagtcgaac ggtaacaggt cttcggacgc 60
tgacgagtgg cgaacgggtg agtaatacat cggaacgtgc ccagtcgtgg gggataacta 120
ctcgaaagag tagctaatac cgcatacgat ctgaggatga aagcggggga ccttcgggcc 180
tcgcgcgatt ggagcggccg atggcagatt aggtagttgg tgggataaaa gcttaccaag 240
ccgacgatct gtagctggtc tgagaggacg accagccaca ctgggactga gacacggccc 300
agactcctac gggaggcagc agtggggaat tttggacaat gggcgaaagc ctgatccagc 360
aatgccgcgt gcaggatgaa ggccttcggg ttgtaaactg cttttgtacg gaacgaaaaa 420
gctccttcta atacaggggg cccatgacgg taccgtaaga ataagcaccg gctaactacg 480
tgccagcagc cgcggtaata cgtagggtgc gagcgttaat cggaattact gggcgtaaag 540
cgtgcgcagg cggttatgta agacagatgt gaaatccccg ggctcaacct gggaactgca 600
tttgtgactg catggctaga gtacggtaga gggggatgga attccgcgtg tagcagtgaa 660
atgcgtagat atgcggagga acaccgatgg cgaaggcaat cccctggacc tgtactgacg 720
ctcatgcacg aaagcgtggg gagcaaacag gattagatac cctggtagtc cacgccctaa 780
acgatgtcaa ctggttgttg ggaattagtt ttctcagtaa cgaagctaac gcgtgaagtt 840
gaccgcctgg ggagtacggc cgcaaggttg aaactcaaag gaattgacgg ggacccgcac 900
aagcggtgga tgatgtggtt taattcgatg caacgcgaaa aaccttaccc acctttgaca 960
tggcaggaag tttccagaga tggattcgtg ctcgaaagag aacctgcaca caggtgctgc 1020
atggctgtcg tcagctcgtg tcgtgagatg ttgggttaag tcccgcaacg agcgcaaccc 1080
ttgtcattag ttgctacatt cagttgagca ctctaatgag actgccggtg acaaaccgga 1140
ggaaggtggg gatgacgtca agtcctcatg gcccttatag gtggggctac acacgtcata 1200
caatggctgg tacagagggt tgccaacccg cgagggggag ctaatcccat aaaaccagtc 1260
gtagtccgga tcgcagtctg caactcgact gcgtgaagtc ggaatcgcta gtaatcgcgg 1320
atcagcatgc cgcggtgaat acgttcccgg gtcttgtaca caccgcccgt cacaccatgg 1380
gagcgggtct cgccagaagt aggtagccta accgcaagga gggcgcttac cacggcgggg 1440
ttcgtgactg gggtgaag 1458

<210> SEQ ID NO 2
<211> LENGTH: 1446
<212> TYPE: DNA
<213> ORGANISM: Pseudarthrobacter sp.

<400> SEQUENCE: 2
gatgaacgct ggcggcgtgc ttaacacatg caagtcgaac gatgatgccc acttgtgggt 60
ggattagtgg cgaacgggtg agtaacacgt gagtaacctg cccttgactc tgggataagc 120
ctgggaaact gggtctaata ccggatatga ctgactatcg catggtggtt ggtggaaagc 180
ttttgcggtt ttggatggac tcgcggccta tcagcttgtt ggtggggtaa tggcctacca 240
aggcgacgac gggtagccgg cctgagaggg tgaccggcca cactgggact gagacacggc 300
ccagactcct acgggaggca gcagtgggga atattgcaca atgggcggaa gcctgatgca 360
gcgacgccgc gtgagggatg acggccttcg ggttgtaaac ctctttcagt agggaagaag 420
cgtaagtgac ggtacctgca gaagaagcgc cggctaacta cgtgccagca gccgcggtaa 480
tacgtagggc gcaagcgtta tccggaatta ttgggcgtaa agagctcgta ggcggtttgt 540
cgcgtctgcc gtgaaagtcc ggggctcaac tccggatctg cggtgggtac gggcagacta 600
gagtgatgta ggggagactg gaattcctgg tgtagcggtg aaatgcgcag atatcaggag 660
gaacaccgat ggcgaaggca ggtctctggg cattaactga cgctgaggag cgaaagcatg 720
gggagcgaac aggattagat accctggtag tccatgccgt aaacgttggg cactaggtgt 780
gggggacatt ccacgttttc cgcgccgtag ctaacgcatt aagtgccccg cctggggagt 840
acggccgcaa ggctaaaact caaaggaatt gacgggggcc cgcacaagcg gcggagcatg 900
cggattaatt cgatgcaacg cgaagaacct taccaaggct tgacatgaac cggaaacgcc 960
tggaaacagg tgccccactt gtggtcggtt tacaggtggt gcatggttgt cgtcagctcg 1020
tgtcgtgaga tgttgggtta agtcccgcaa cgagcgcaac cctcgttcta tgttgccagc 1080
acgtgatggt ggggactcat aggagactgc cggggtcaac tcggaggaag gtggggacga 1140
cgtcaaatca tcatgcccct tatgtcttgg gcttcacgca tgctacaatg gccggtacaa 1200
agggttgcga tactgtgagg tggagctaat cccaaaaagc cggtctcagt tcggattggg 1260
gtctgcaact cgaccccatg aagtcggagt cgctagtaat cgcagatcag caacgctgcg 1320
gtgaatacgt tcccgggcct tgtacacacc gcccgtcaag tcacgaaagt tggtaacacc 1380
cgaagccggt ggcctaaccc ttttgggggg gagccgtcga aggtgggact ggcgattggg 1440
actaag 1446

<210> SEQ ID NO 3
<211> LENGTH: 1462
<212> TYPE: DNA
<213> ORGANISM: Pseudomonas sp.

<400> SEQUENCE: 3
attgaacgct ggcggcaggc ctaacacatg caagtcgagc ggatgatggg agcttgctcc 60
cggattcagc ggcggacggg tgagtaatgc ctaggaatct gcctggtagt gggggacaac 120
gtttcgaaag gaacgctaat accgcatacg tcctacggga gaaagcaggg gaccttcggg 180
ccttgcgcta tcagatgagc ctaggtcgga ttagctagtt ggtggggtaa aggcctacca 240
aggcgacgat ccgtaactgg tctgagagga tgatcagtca cactggaact gagacacggt 300
ccagactcct acgggaggca gcagtgggga atattggaca atgggcgaaa gcctgatcca 360
gccatgccgc gtgtgtgaag aaggtcttcg gattgtaaag cactttaagt tgggaggaag 420
ggcagtaagt taataccttg ctgttttgac gttaccaaca gaataagcac cggctaactt 480
cgtgccagca gccgcggtaa tacgaagggt gcaagcgtta atcggaatta ctgggcgtaa 540
agcgcgcgta ggtggtttgg taagatggat gtgaaatccc cgggctcaac ctgggaactg 600
catccataac tgcctgacta gagtacggta gagggtggtg gaatttcctg tgtagcggtg 660
aaatgcgtag atataggaag gaacaccagt ggcgaaggcg accacctgga ctgatactga 720
cactgaggtg cgaaagcgtg gggagcaaac aggattagat accctggtag tccacgccgt 780
aaacgatgtc gactagccgt tgggatcctt gagatcttag tggcgcagct aacgcgataa 840
gtcgaccgcc tggggagtac ggccgcaagg ttaaaactca aatgaattga cgggggcccg 900
cacaagcggt ggagcatgtg gtttaattcg aagcaacgcg aagaacctta cctggccttg 960
acatgtccgg aatcttgcag agatgcgaga gtgccttcgg gaatcggaac acaggtgctg 1020
catggctgtc gtcagctcgt gtcgtgagat gttgggttaa gtcccgtaac gagcgcaacc 1080
cttgtcctta gttaccagca cgttatggtg ggcactctaa ggagactgcc ggtgacaaac 1140
cggaggaagg tggggatgac gtcaagtcat catggccctt acggccaggg ctacacacgt 1200

-continued

| | | | | | | |
|---|---|---|---|---|---|---|
| gctacaatgg | tcggtacaga | gggttgccaa | gccgcgaggt | ggagctaatc | ccataaaacc | 1260 |
| gatcgtagtc | cggatcgcag | tctgcaactc | gactgcgtga | agtcggaatc | gctagtaatc | 1320 |
| gtgaatcaga | atgtcacggt | gaatacgttc | ccgggccttg | tacacaccgc | ccgtcacacc | 1380 |
| atgggagtgg | gttgctccag | aagtagctag | tctaaccgca | agggggacgg | ttaccacgga | 1440 |
| gtgattcatg | actggggtga | ag | | | | 1462 |